(12) United States Patent
Flanagan

(10) Patent No.: US 8,089,029 B2
(45) Date of Patent: Jan. 3, 2012

(54) BIOABSORBABLE METAL MEDICAL DEVICE AND METHOD OF MANUFACTURE

(75) Inventor: Aiden Flanagan, Galway (IE)

(73) Assignee: Boston Scientific SciMed, Inc., Maple Grove, MN (US)

( * ) Notice: Subject to any disclaimer, the term of this patent is extended or adjusted under 35 U.S.C. 154(b) by 1297 days.

(21) Appl. No.: 11/344,761

(22) Filed: Feb. 1, 2006

(65) Prior Publication Data

US 2007/0178129 A1    Aug. 2, 2007

(51) Int. Cl.
    *B23K 26/38* (2006.01)
(52) U.S. Cl. .............. 219/121.7; 420/402; 420/403; 420/407; 420/408
(58) Field of Classification Search .......... 420/402, 420/403, 407, 408; 623/1.15; 148/403
    See application file for complete search history.

(56) References Cited

U.S. PATENT DOCUMENTS

| | | | |
|---|---|---|---|
| 2,950,187 A | 8/1960 | Ototani | |
| 3,560,362 A * | 2/1971 | Kasamatsu et al. | 522/6 |
| 3,569,660 A | 3/1971 | Houldcroft | 219/121 |
| 3,687,135 A | 8/1972 | Stroganov et al. | |
| 3,758,396 A | 9/1973 | Vieth et al. | |
| 3,868,578 A | 2/1975 | Oldham | |
| 3,910,819 A | 10/1975 | Rembaum et al. | |
| 3,948,254 A | 4/1976 | Zaffaroni | |
| 3,952,334 A | 4/1976 | Bokros et al. | |
| 3,993,072 A | 11/1976 | Zaffaroni | |
| 4,002,877 A | 1/1977 | Banas | 219/121 LM |
| 4,101,984 A | 7/1978 | MacGregor | |
| 4,143,661 A | 3/1979 | LaForge et al. | |
| 4,202,055 A | 5/1980 | Reiner et al. | |
| 4,237,559 A | 12/1980 | Borom | |
| 4,308,868 A | 1/1982 | Jhabvala | |
| 4,334,327 A | 6/1982 | Lyman et al. | |
| 4,401,546 A | 8/1983 | Nakamura et al. | |
| 4,532,929 A | 8/1985 | Mattei et al. | |
| 4,539,061 A | 9/1985 | Sagiv | |
| 4,542,539 A | 9/1985 | Rowe et al. | |
| 4,585,652 A | 4/1986 | Miller et al. | |
| 4,634,502 A | 1/1987 | Callahan et al. | |
| 4,655,771 A | 4/1987 | Wallsten | |
| 4,657,544 A | 4/1987 | Pinchuk | |
| 4,665,896 A | 5/1987 | LaForge et al. | |
| 4,705,502 A | 11/1987 | Patel | |
| 4,713,070 A | 12/1987 | Mano | |
| 4,725,273 A | 2/1988 | Kira | |

(Continued)

FOREIGN PATENT DOCUMENTS

AU    739 507    11/1998

(Continued)

OTHER PUBLICATIONS

U.S. Appl. No. 10/849,742, filed May 20, 2004, Chen et al.

(Continued)

*Primary Examiner* — Jie Yang
(74) *Attorney, Agent, or Firm* — Fish & Richardson P.C.

(57) ABSTRACT

A method and apparatus is provided for processing a medical device formed from a bioabsorbable metallic material. The method begins by generating a beam of radiation onto the bioabsorbable metallic material. The radiation beam is transmitted through a fluid medium and onto a heat affected zone (HAZ) of the bioabsorbable metallic material to thereby cool the HAZ and reduce a concentration of oxygen surrounding the HAZ.

20 Claims, 1 Drawing Sheet

U.S. PATENT DOCUMENTS

| | | | |
|---|---|---|---|
| 4,733,665 A | 3/1988 | Palmaz | |
| 4,767,418 A | 8/1988 | Deininger et al. | |
| 4,784,659 A | 11/1988 | Fleckenstein et al. | |
| 4,800,882 A | 1/1989 | Gianturco | |
| 4,804,382 A | 2/1989 | Turina et al. | |
| 4,886,062 A | 12/1989 | Wiktor | |
| 4,954,126 A | 9/1990 | Wallsten | |
| 4,976,692 A | 12/1990 | Atad | |
| 4,994,071 A | 2/1991 | MacGregor | |
| 5,024,671 A | 6/1991 | Tu et al. | |
| 5,059,211 A | 10/1991 | Stack et al. | |
| 5,061,275 A | 10/1991 | Wallsten et al. | |
| 5,061,914 A | 10/1991 | Busch et al. | |
| 5,073,365 A | 12/1991 | Katz et al. | |
| 5,079,203 A | 1/1992 | Pinnavaia | |
| 5,091,024 A | 2/1992 | DeBold et al. | |
| 5,091,205 A | 2/1992 | Fan | |
| 5,102,403 A | 4/1992 | Alt | |
| 5,120,322 A | 6/1992 | Davis et al. | |
| 5,125,971 A | 6/1992 | Nonami et al. | |
| 5,147,370 A | 9/1992 | McNamara et al. | |
| 5,163,958 A | 11/1992 | Pinchuk | |
| 5,195,969 A | 3/1993 | Wang et al. | |
| 5,205,921 A | 4/1993 | Shirkanzadeh | |
| 5,234,457 A | 8/1993 | Andersen | |
| 5,236,413 A | 8/1993 | Feiring | |
| 5,236,447 A | 8/1993 | Kubo et al. | |
| 5,270,086 A | 12/1993 | Hamlin | |
| 5,279,292 A | 1/1994 | Baumann et al. | |
| 5,290,585 A | 3/1994 | Elton | |
| 5,292,558 A | 3/1994 | Heller et al. | |
| 5,302,414 A | 4/1994 | Alkhimov et al. | |
| 5,304,121 A | 4/1994 | Sahatjian | |
| 5,304,195 A | 4/1994 | Twyford, Jr. et al. | |
| 5,306,286 A | 4/1994 | Stack et al. | |
| 5,314,453 A | 5/1994 | Jeutter | |
| 5,322,520 A | 6/1994 | Milder | |
| 5,342,348 A | 8/1994 | Kaplan | |
| 5,348,553 A | 9/1994 | Whitney | |
| 5,356,433 A | 10/1994 | Rowland et al. | |
| 5,360,440 A | 11/1994 | Andersen | |
| 5,366,504 A | 11/1994 | Andersen et al. | |
| 5,380,298 A | 1/1995 | Zabetakis et al. | |
| 5,383,935 A | 1/1995 | Shirkhanzadeh | |
| 5,385,776 A | 1/1995 | Maxfield et al. | |
| 5,397,307 A | 3/1995 | Goodin | |
| 5,405,367 A | 4/1995 | Schulman et al. | |
| 5,421,955 A | 6/1995 | Lau et al. | 216/48 |
| 5,439,446 A | 8/1995 | Barry | |
| 5,443,458 A | 8/1995 | Eury | |
| 5,443,496 A | 8/1995 | Schwartz et al. | |
| 5,443,500 A | 8/1995 | Sigwart | |
| 5,449,373 A | 9/1995 | Pinchasik et al. | |
| 5,449,382 A | 9/1995 | Dayton | |
| 5,458,627 A | 10/1995 | Baranowski, Jr. et al. | |
| 5,462,575 A | 10/1995 | Del Corso | |
| 5,464,450 A | 11/1995 | Buscemi et al. | |
| 5,464,650 A | 11/1995 | Berg et al. | |
| 5,468,574 A | 11/1995 | Ehrenberg et al. | |
| 5,474,797 A | 12/1995 | Sioshansi et al. | |
| 5,500,013 A | 3/1996 | Buscemi et al. | |
| 5,514,154 A | 5/1996 | Lau et al. | 606/195 |
| 5,527,337 A | 6/1996 | Stack et al. | |
| 5,536,573 A | 7/1996 | Rubner et al. | |
| 5,545,208 A | 8/1996 | Wolff et al. | |
| 5,549,664 A | 8/1996 | Hirata et al. | |
| 5,551,954 A | 9/1996 | Buscemi et al. | |
| 5,578,075 A | 11/1996 | Dayton | |
| 5,587,200 A | 12/1996 | Lorenz et al. | |
| 5,587,507 A | 12/1996 | Kohn et al. | |
| 5,591,222 A | 1/1997 | Susawa et al. | |
| 5,591,224 A | 1/1997 | Schwartz et al. | |
| 5,599,352 A | 2/1997 | Dinh et al. | |
| 5,603,556 A | 2/1997 | Klink | |
| 5,605,696 A | 2/1997 | Eury et al. | |
| 5,607,463 A | 3/1997 | Schwartz et al. | |
| 5,609,629 A | 3/1997 | Fearnot et al. | |
| 5,614,549 A | 3/1997 | Greenwald et al. | |
| 5,624,411 A | 4/1997 | Tuch | |
| 5,628,787 A | 5/1997 | Mayer | |
| 5,629,077 A | 5/1997 | Turnlund et al. | |
| 5,632,771 A | 5/1997 | Boatman et al. | |
| 5,632,840 A | 5/1997 | Campbell | |
| 5,649,951 A | 7/1997 | Davidson | |
| 5,658,327 A | 8/1997 | Altman et al. | |
| 5,674,192 A | 10/1997 | Sahatjian et al. | |
| 5,674,242 A | 10/1997 | Phan | |
| 5,676,685 A | 10/1997 | Razavi | |
| 5,679,440 A | 10/1997 | Kubota | |
| 5,690,670 A | 11/1997 | Davidson | |
| 5,693,085 A | 12/1997 | Buirge et al. | |
| 5,693,928 A | 12/1997 | Egitto et al. | |
| 5,697,967 A | 12/1997 | Dinh et al. | |
| 5,700,286 A | 12/1997 | Tartaglia et al. | |
| 5,716,981 A | 2/1998 | Hunter et al. | |
| 5,721,049 A | 2/1998 | Marcolongo et al. | |
| 5,725,570 A | 3/1998 | Heath | |
| 5,733,925 A | 3/1998 | Kunz et al. | |
| 5,741,331 A | 4/1998 | Pinchuk | |
| 5,744,515 A | 4/1998 | Clapper | |
| 5,749,809 A | 5/1998 | Lin | |
| 5,749,880 A | 5/1998 | Banas et al. | |
| 5,758,562 A | 6/1998 | Thompson | |
| 5,759,192 A | 6/1998 | Saunders | 606/194 |
| 5,761,775 A | 6/1998 | Legome et al. | |
| 5,769,883 A | 6/1998 | Buscemi et al. | |
| 5,769,884 A | 6/1998 | Solovay | |
| 5,773,925 A | 6/1998 | Kimura et al. | |
| 5,776,184 A | 7/1998 | Tuch | |
| 5,779,904 A | 7/1998 | Ruderman et al. | |
| 5,780,807 A | 7/1998 | Saunders | 219/121.71 |
| 5,788,626 A | 8/1998 | Thompson | |
| 5,788,687 A | 8/1998 | Batich et al. | |
| 5,788,979 A | 8/1998 | Alt et al. | |
| 5,797,898 A | 8/1998 | Santini, Jr. et al. | |
| 5,800,511 A | 9/1998 | Mayer | |
| 5,815,904 A | 10/1998 | Clubb et al. | |
| 5,817,046 A | 10/1998 | Glickman | |
| 5,824,045 A | 10/1998 | Alt | |
| 5,824,048 A | 10/1998 | Tuch | |
| 5,824,077 A | 10/1998 | Mayer | |
| 5,830,217 A | 11/1998 | Ryan | |
| 5,833,715 A | 11/1998 | Vachon et al. | |
| 5,837,007 A | 11/1998 | Altman et al. | |
| 5,837,275 A | 11/1998 | Burrell et al. | |
| 5,840,387 A | 11/1998 | Berlowitz-Tarrant et al. | |
| 5,843,089 A | 12/1998 | Sahatjian et al. | |
| 5,843,172 A | 12/1998 | Yan | |
| 5,852,277 A | 12/1998 | Gustafson | 219/121.67 |
| 5,854,382 A | 12/1998 | Loomis | |
| 5,858,556 A | 1/1999 | Eckert et al. | |
| 5,869,140 A | 2/1999 | Blohowiak et al. | |
| 5,873,904 A | 2/1999 | Ragheb et al. | |
| 5,876,756 A | 3/1999 | Takada et al. | |
| 5,879,697 A | 3/1999 | Ding et al. | |
| 5,880,661 A | 3/1999 | Davidson et al. | |
| 5,882,335 A | 3/1999 | Leone et al. | |
| 5,891,108 A | 4/1999 | Leone et al. | |
| 5,891,191 A | 4/1999 | Stinson | |
| 5,899,935 A | 5/1999 | Ding | |
| 5,902,266 A | 5/1999 | Leone et al. | |
| 5,906,759 A | 5/1999 | Richter | 219/121.63 |
| 5,907,893 A | 6/1999 | Zadno-Azizi et al. | |
| 5,922,005 A | 7/1999 | Richter et al. | 606/192 |
| 5,922,021 A | 7/1999 | Jang | |
| 5,928,247 A | 7/1999 | Barry et al. | |
| 5,935,506 A | 8/1999 | Schmitz et al. | |
| 5,938,903 A | 8/1999 | Broderick | |
| 5,941,843 A | 8/1999 | Atanasoska et al. | |
| 5,951,458 A | 9/1999 | Hastings et al. | |
| 5,951,881 A | 9/1999 | Rogers et al. | |
| 5,954,706 A | 9/1999 | Sahatjian | |
| 5,957,975 A | 9/1999 | Lafont et al. | |
| 5,958,440 A | 9/1999 | Burrell et al. | |
| 5,961,547 A | 10/1999 | Razavi | |
| 5,968,091 A | 10/1999 | Pinchuk et al. | |
| 5,968,092 A | 10/1999 | Buscemi et al. | |

| | | | | | | |
|---|---|---|---|---|---|---|
| 5,972,027 | A | 10/1999 | Johnson | 6,277,078 | B1 | 8/2001 | Porat et al. |
| 5,972,192 | A | 10/1999 | Dubin et al. | 6,280,385 | B1 | 8/2001 | Melzer et al. |
| 5,976,169 | A | 11/1999 | Imran | 6,280,411 | B1 | 8/2001 | Lennox |
| 5,976,454 | A | 11/1999 | Sterzel et al. | 6,283,386 | B1 | 9/2001 | Van Steenkiste et al. |
| 5,977,204 | A | 11/1999 | Boyan et al. | 6,287,331 | B1 | 9/2001 | Heath |
| 5,980,554 | A | 11/1999 | Lenker et al. | 6,287,332 | B1 | 9/2001 | Bolz et al. ............... 623/1.15 |
| 5,980,564 | A | 11/1999 | Stinson | 6,287,335 | B1 | 9/2001 | Drasler et al. |
| 5,980,566 | A | 11/1999 | Alt et al. | 6,287,628 | B1 | 9/2001 | Hossainy et al. |
| 6,001,125 | A | 12/1999 | Golds et al. | 6,290,721 | B1 | 9/2001 | Heath |
| 6,013,591 | A | 1/2000 | Ying et al. | 6,290,722 | B1 | 9/2001 | Wang |
| 6,017,553 | A | 1/2000 | Burrell et al. | 6,291,076 | B1 | 9/2001 | Nakatsugawa |
| 6,017,577 | A | 1/2000 | Hostettler et al. | 6,299,604 | B1 | 10/2001 | Ragheb et al. |
| 6,021,347 | A | 2/2000 | Herbst et al. | 6,299,755 | B1 | 10/2001 | Richter |
| 6,025,036 | A | 2/2000 | McGill et al. | 6,306,144 | B1 | 10/2001 | Sydney et al. |
| 6,027,742 | A | 2/2000 | Lee et al. | 6,309,414 | B1 | 10/2001 | Rolando et al. |
| 6,034,295 | A | 3/2000 | Rehberg et al. | 6,312,463 | B1 | 11/2001 | Rourke et al. |
| 6,042,597 | A | 3/2000 | Kveen et al. | 6,315,708 | B1 | 11/2001 | Salmon et al. |
| 6,056,776 | A | 5/2000 | Lau et al. | 6,323,146 | B1 | 11/2001 | Pugh et al. |
| 6,063,101 | A | 5/2000 | Jacobsen et al. | 6,325,825 | B1 | 12/2001 | Kula et al. |
| 6,071,305 | A | 6/2000 | Brown et al. | 6,327,504 | B1 | 12/2001 | Dolgin et al. |
| 6,080,190 | A | 6/2000 | Schwartz | 6,331,312 | B1 | 12/2001 | Lee et al. |
| 6,086,773 | A | 7/2000 | Dufresne et al. | 6,335,029 | B1 | 1/2002 | Kamath et al. |
| 6,096,070 | A | 8/2000 | Ragheb et al. | 6,337,076 | B1 | 1/2002 | Studin |
| 6,096,175 | A | 8/2000 | Roth | 6,338,739 | B1 | 1/2002 | Datta et al. |
| 6,099,561 | A | 8/2000 | Alt | 6,342,507 | B1 | 1/2002 | Naicker et al. |
| 6,099,562 | A | 8/2000 | Ding et al. | 6,344,055 | B1 | 2/2002 | Shukov |
| 6,106,473 | A | 8/2000 | Violante et al. | 6,348,960 | B1 | 2/2002 | Etori et al. |
| 6,107,004 | A | 8/2000 | Donadio, III | 6,358,276 | B1 | 3/2002 | Edwin |
| 6,117,592 | A | 9/2000 | Hoshino et al. | 6,364,823 | B1 | 4/2002 | Garibaldi et al. |
| 6,120,260 | A | 9/2000 | Jirele | 6,364,856 | B1 | 4/2002 | Ding et al. |
| 6,120,535 | A | 9/2000 | McDonald et al. | 6,364,903 | B2 | 4/2002 | Tseng et al. |
| 6,120,660 | A | 9/2000 | Chu et al. | 6,366,808 | B1 | 4/2002 | Schroeppel et al. |
| 6,123,861 | A | 9/2000 | Santini, Jr. et al. | 6,368,658 | B1 | 4/2002 | Schwarz et al. |
| 6,132,463 | A | 10/2000 | Lee et al. | 6,369,355 | B1 | 4/2002 | Saunders |
| 6,139,573 | A | 10/2000 | Sogard et al. | 6,375,826 | B1 | 4/2002 | Wang et al. |
| 6,139,574 | A | 10/2000 | Vacanti et al. | 6,379,379 | B1 | 4/2002 | Wang |
| 6,139,913 | A | 10/2000 | Van Steenkiste et al. | 6,379,382 | B1 | 4/2002 | Yang et al. |
| 6,140,740 | A | 10/2000 | Porat et al. | 6,379,383 | B1 | 4/2002 | Palmaz et al. |
| 6,143,370 | A | 11/2000 | Panagiotou et al. | 6,379,392 | B1 | 4/2002 | Walak ............... 623/23.7 |
| 6,153,252 | A | 11/2000 | Hossainy et al. | 6,383,214 | B1 | 5/2002 | Banas et al. |
| 6,159,142 | A | 12/2000 | Alt | 6,387,121 | B1 | 5/2002 | Alt |
| 6,162,238 | A | 12/2000 | Kaplan et al. | 6,387,124 | B1 | 5/2002 | Buscemi et al. |
| 6,164,284 | A | 12/2000 | Schulman et al. | 6,390,967 | B1 | 5/2002 | Forman et al. |
| 6,165,211 | A | 12/2000 | Thompson | 6,391,033 | B2 | 5/2002 | Ryan |
| 6,167,307 | A | 12/2000 | Hess | 6,391,052 | B2 | 5/2002 | Bulrge et al. |
| 6,168,602 | B1 | 1/2001 | Ryan | 6,395,326 | B1 | 5/2002 | Castro et al. |
| 6,170,488 | B1 | 1/2001 | Spillman, Jr. et al. | 6,398,806 | B1 | 6/2002 | You |
| 6,174,329 | B1 | 1/2001 | Callol et al. | 6,409,754 | B1 | 6/2002 | Smith et al. |
| 6,174,330 | B1 | 1/2001 | Stinson | 6,419,692 | B1 | 7/2002 | Yang et al. |
| 6,180,222 | B1 | 1/2001 | Schulz et al. | 6,423,092 | B2 | 7/2002 | Datta et al. |
| 6,185,455 | B1 | 2/2001 | Loeb et al. | 6,425,855 | B2 | 7/2002 | Tomonto |
| 6,185,457 | B1 | 2/2001 | Kroll et al. | 6,436,133 | B1 | 8/2002 | Furst et al. |
| 6,190,404 | B1 | 2/2001 | Palmaz et al. | 6,440,166 | B1 | 8/2002 | Kolluri |
| 6,192,271 | B1 | 2/2001 | Hayman | 6,440,487 | B1 | 8/2002 | Delfino et al. |
| 6,201,991 | B1 | 3/2001 | Chekanov | 6,440,503 | B1 | 8/2002 | Merdan et al. ............... 427/561 |
| 6,203,536 | B1 | 3/2001 | Berg et al. | 6,447,540 | B1 | 9/2002 | Fontaine et al. |
| 6,206,914 | B1 | 3/2001 | Soykan et al. | 6,451,871 | B1 | 9/2002 | Winterton et al. |
| 6,206,915 | B1 | 3/2001 | Fagan et al. | 6,458,153 | B1 | 10/2002 | Bailey et al. |
| 6,206,916 | B1 | 3/2001 | Furst | 6,468,304 | B1 | 10/2002 | Dubois-Rande et al. |
| 6,212,434 | B1 | 4/2001 | Scheiner | 6,471,721 | B1 | 10/2002 | Dang |
| 6,214,037 | B1 | 4/2001 | Mitchell et al. | 6,471,980 | B2 | 10/2002 | Sirhan et al. |
| 6,214,042 | B1 | 4/2001 | Jacobsen et al. | 6,475,477 | B1 | 11/2002 | Kohn et al. |
| 6,217,607 | B1 | 4/2001 | Alt | 6,478,815 | B1 | 11/2002 | Alt |
| 6,231,597 | B1 | 5/2001 | Deem et al. | 6,479,146 | B1 | 11/2002 | Caruso et al. |
| 6,240,616 | B1 | 6/2001 | Yan | 6,486,588 | B2 | 11/2002 | Doron |
| 6,241,762 | B1 | 6/2001 | Shanley | 6,488,702 | B1 | 12/2002 | Besselink |
| 6,245,103 | B1 | 6/2001 | Stinson | 6,491,666 | B1 | 12/2002 | Santini, Jr. et al. |
| 6,245,104 | B1 | 6/2001 | Alt | 6,491,720 | B1 | 12/2002 | Vallana et al. |
| 6,249,952 | B1 | 6/2001 | Ding | 6,492,096 | B1 | 12/2002 | Liu et al. |
| 6,251,136 | B1 | 6/2001 | Guruwaiya et al. | 6,503,556 | B2 | 1/2003 | Harish et al. |
| 6,251,980 | B1 | 6/2001 | Lan et al. | 6,503,921 | B2 | 1/2003 | Naicker et al. |
| 6,253,252 | B1 | 6/2001 | Schofield | 6,506,437 | B1 | 1/2003 | Harish et al. |
| 6,253,443 | B1 | 7/2001 | Johnson | 6,506,972 | B1 | 1/2003 | Wang |
| 6,254,632 | B1 | 7/2001 | Wu et al. | 6,514,283 | B2 | 2/2003 | DiMatteo et al. |
| 6,258,117 | B1 | 7/2001 | Camrud et al. | 6,517,571 | B1 | 2/2003 | Brauker et al. |
| 6,264,687 | B1 | 7/2001 | Tomonto | 6,517,888 | B1 | 2/2003 | Weber |
| 6,270,831 | B2 | 8/2001 | Kumar et al. | 6,524,274 | B1 | 2/2003 | Rosenthal et al. |
| 6,273,908 | B1 | 8/2001 | Ndondo-Lay | 6,524,334 | B1 | 2/2003 | Thompson |
| 6,273,913 | B1 | 8/2001 | Wright et al. | 6,527,801 | B1 | 3/2003 | Dutta |

| | | |
|---|---|---|
| 6,527,938 B2 | 3/2003 | Bales et al. |
| 6,530,949 B2 | 3/2003 | Konya et al. |
| 6,530,951 B1 | 3/2003 | Bates et al. |
| 6,537,310 B1 | 3/2003 | Palmaz et al. |
| 6,537,312 B2 | 3/2003 | Datta et al. |
| 6,544,582 B1 | 4/2003 | Yoe |
| 6,545,097 B2 | 4/2003 | Pinchuk et al. |
| 6,549,811 B2 | 4/2003 | Stewart et al. |
| 6,554,854 B1 | 4/2003 | Flanagan ............... 623/121.72 |
| 6,558,422 B1 | 5/2003 | Baker et al. |
| 6,558,733 B1 | 5/2003 | Hossainy et al. |
| 6,565,602 B2 | 5/2003 | Rolando et al. |
| 6,569,489 B1 | 5/2003 | Li |
| 6,584,349 B1 | 6/2003 | Sage et al. |
| 6,585,764 B2 | 7/2003 | Wright et al. |
| 6,585,765 B1 | 7/2003 | Hossainy et al. |
| 6,586,705 B1 * | 7/2003 | Schell ...................... 219/121.67 |
| 6,589,286 B1 | 7/2003 | Litner |
| 6,599,558 B1 | 7/2003 | Al-Lamee et al. |
| 6,602,287 B1 | 8/2003 | Millare et al. |
| 6,607,598 B2 | 8/2003 | Schwarz et al. |
| 6,613,077 B2 | 9/2003 | Gilligan et al. |
| 6,613,083 B2 | 9/2003 | Alt |
| 6,613,432 B2 | 9/2003 | Zamora et al. |
| 6,616,765 B1 | 9/2003 | Castro et al. |
| 6,626,933 B1 | 9/2003 | Lau et al. |
| 6,626,936 B2 | 9/2003 | Stinson |
| 6,626,939 B1 | 9/2003 | Burnside et al. |
| 6,627,321 B1 | 9/2003 | Ellingsen et al. |
| 6,628,989 B1 | 9/2003 | Penner |
| 6,629,992 B2 | 10/2003 | Bigus et al. |
| 6,635,082 B1 | 10/2003 | Hossainy et al. |
| 6,638,302 B1 | 10/2003 | Curcio et al. |
| 6,641,607 B1 | 11/2003 | Hossainy et al. |
| 6,652,575 B2 | 11/2003 | Wang |
| 6,652,578 B2 | 11/2003 | Bailey et al. |
| 6,652,581 B1 | 11/2003 | Ding |
| 6,652,582 B1 | 11/2003 | Stinson |
| 6,660,034 B1 | 12/2003 | Mandrusov et al. |
| 6,663,662 B2 | 12/2003 | Pacetti et al. |
| 6,663,664 B1 | 12/2003 | Pacetti |
| 6,669,980 B2 | 12/2003 | Hansen |
| 6,673,105 B1 | 1/2004 | Chen |
| 6,673,385 B1 | 1/2004 | Ding et al. |
| 6,673,999 B1 | 1/2004 | Wang et al. |
| 6,676,987 B2 | 1/2004 | Zhong |
| 6,676,989 B2 | 1/2004 | Kirkpatrick et al. |
| 6,689,160 B1 | 2/2004 | Okuda et al. |
| 6,689,803 B2 | 2/2004 | Hunter |
| 6,695,865 B2 | 2/2004 | Boyle et al. |
| 6,696,666 B2 | 2/2004 | Merdan et al. ............ 219/121.7 |
| 6,696,667 B1 | 2/2004 | Flanagan ............... 219/121.72 |
| 6,699,281 B2 | 3/2004 | Vallana et al. |
| 6,699,282 B1 | 3/2004 | Sceusa |
| 6,709,379 B1 | 3/2004 | Brandau et al. |
| 6,709,397 B2 | 3/2004 | Taylor |
| 6,709,451 B1 | 3/2004 | Noble et al. |
| 6,710,053 B2 | 3/2004 | Naicker et al. |
| 6,712,844 B2 | 3/2004 | Pacetti |
| 6,712,845 B2 | 3/2004 | Hossainy |
| 6,713,671 B1 | 3/2004 | Wang et al. |
| 6,716,444 B1 | 4/2004 | Castro et al. |
| 6,719,987 B2 | 4/2004 | Burrell et al. |
| 6,720,402 B2 | 4/2004 | Langer et al. |
| 6,723,120 B2 | 4/2004 | Yan |
| 6,723,350 B2 | 4/2004 | Burrell et al. |
| 6,725,901 B1 | 4/2004 | Kramer et al. |
| 6,726,712 B1 | 4/2004 | Raeder-Devens |
| 6,730,117 B1 | 5/2004 | Tseng et al. |
| 6,730,120 B2 | 5/2004 | Berg et al. |
| 6,730,699 B2 | 5/2004 | Li et al. |
| 6,733,513 B2 | 5/2004 | Boyle et al. |
| 6,740,077 B1 | 5/2004 | Brandau et al. |
| 6,743,388 B2 | 6/2004 | Sridharan et al. |
| 6,752,826 B2 | 6/2004 | Holloway et al. |
| 6,752,829 B2 | 6/2004 | Kocur et al. |
| 6,753,071 B1 | 6/2004 | Pacetti |
| 6,758,859 B1 | 7/2004 | Dang et al. |
| 6,764,505 B1 | 7/2004 | Hossainy et al. |
| 6,764,579 B2 | 7/2004 | Veerasamy et al. |
| 6,764,709 B2 | 7/2004 | Flanagan |
| 6,765,144 B1 | 7/2004 | Wang et al. |
| 6,767,360 B1 | 7/2004 | Alt et al. |
| 6,770,086 B1 | 8/2004 | Girton |
| 6,770,729 B2 | 8/2004 | Van Antwerp |
| 6,774,278 B1 | 8/2004 | Ragheb et al. |
| 6,776,022 B2 | 8/2004 | Kula et al. |
| 6,776,094 B1 | 8/2004 | Whitesides et al. |
| 6,776,793 B2 | 8/2004 | Brown et al. |
| 6,780,424 B2 | 8/2004 | Claude |
| 6,783,543 B2 | 8/2004 | Jang |
| 6,790,228 B2 | 9/2004 | Hossainy et al. |
| 6,793,877 B1 | 9/2004 | Pettersen et al. |
| 6,796,435 B2 | 9/2004 | Izumi |
| 6,803,070 B2 | 10/2004 | Weber |
| 6,805,709 B1 | 10/2004 | Schaldach et al. |
| 6,805,898 B1 | 10/2004 | Wu et al. |
| 6,807,440 B2 | 10/2004 | Weber |
| RE38,653 E | 11/2004 | Igaki et al. |
| 6,815,609 B1 | 11/2004 | Wang et al. |
| 6,820,676 B2 | 11/2004 | Palmaz et al. |
| 6,827,737 B2 | 12/2004 | Hill et al. |
| 6,827,966 B2 | 12/2004 | Qiu et al. |
| 6,833,004 B2 | 12/2004 | Ishii et al. |
| 6,846,323 B2 | 1/2005 | Yip et al. |
| 6,846,841 B2 | 1/2005 | Hunter et al. |
| 6,847,837 B1 | 1/2005 | Melzer et al. |
| 6,849,085 B2 | 2/2005 | Marton |
| 6,849,089 B2 | 2/2005 | Stoll |
| 6,852,122 B2 | 2/2005 | Rush |
| 6,854,172 B2 | 2/2005 | Kaese et al. |
| 6,861,088 B2 | 3/2005 | Weber et al. |
| 6,865,810 B2 | 3/2005 | Stinson |
| 6,866,805 B2 | 3/2005 | Hong et al. |
| 6,869,443 B2 | 3/2005 | Buscemi et al. |
| 6,869,701 B1 | 3/2005 | Aita et al. |
| 6,875,227 B2 | 4/2005 | Yoon |
| 6,878,249 B2 | 4/2005 | Kouyama et al. |
| 6,884,429 B2 | 4/2005 | Koziak et al. |
| 6,887,270 B2 | 5/2005 | Miller et al. |
| 6,887,857 B2 | 5/2005 | Naimark et al. |
| 6,896,697 B1 | 5/2005 | Yip et al. |
| 6,899,731 B2 | 5/2005 | Li et al. |
| 6,899,914 B2 | 5/2005 | Schaldach et al. |
| 6,904,658 B2 | 6/2005 | Hines |
| 6,908,506 B2 | 6/2005 | Zimmermann |
| 6,908,622 B2 | 6/2005 | Barry et al. |
| 6,908,624 B2 | 6/2005 | Hossainy et al. |
| 6,913,617 B1 | 7/2005 | Reiss |
| 6,913,765 B2 | 7/2005 | Li et al. |
| 6,918,869 B2 | 7/2005 | Shaw et al. |
| 6,918,927 B2 | 7/2005 | Bates et al. |
| 6,921,390 B2 | 7/2005 | Bucay-Couto et al. |
| 6,923,996 B2 | 8/2005 | Epstein et al. |
| 6,926,735 B2 | 8/2005 | Henderson |
| 6,932,930 B2 | 8/2005 | DeSimone et al. |
| 6,936,066 B2 | 8/2005 | Palmaz et al. |
| 6,939,320 B2 | 9/2005 | Lennox |
| 6,945,993 B2 | 9/2005 | Kveen et al. |
| 6,951,053 B2 | 10/2005 | Padilla et al. |
| 6,953,560 B1 | 10/2005 | Castro et al. |
| 6,953,594 B2 | 10/2005 | Lee et al. |
| 6,954,977 B2 | 10/2005 | Maguire et al. |
| 6,955,661 B1 | 10/2005 | Herweck et al. |
| 6,955,685 B2 | 10/2005 | Escamilla et al. |
| 6,962,822 B2 | 11/2005 | Hart et al. |
| 6,964,817 B2 | 11/2005 | Date et al. |
| 6,971,813 B2 | 12/2005 | Shekalim et al. |
| 6,972,130 B1 | 12/2005 | Lee et al. |
| 6,973,718 B2 | 12/2005 | Sheppard, Jr. et al. |
| 6,979,346 B1 | 12/2005 | Hossainy et al. |
| 6,979,347 B1 | 12/2005 | Wu et al. |
| 6,979,348 B2 | 12/2005 | Sundar |
| 6,981,986 B1 | 1/2006 | Brown et al. |
| 6,984,404 B1 | 1/2006 | Talton et al. |
| 6,986,899 B2 | 1/2006 | Hossainy et al. |
| 6,989,156 B2 | 1/2006 | Gillis |
| 6,991,709 B2 | 1/2006 | Gopalraja et al. |

| | | | |
|---|---|---|---|
| 7,001,421 B2 | 2/2006 | Cheng et al. | |
| 7,004,968 B2 | 2/2006 | Lootz et al. | |
| 7,011,670 B2 | 3/2006 | Radisch, Jr. | |
| 7,011,678 B2 | 3/2006 | Tenerz et al. ............... 623/1.15 | |
| 7,011,680 B2 | 3/2006 | Alt | |
| 7,018,408 B2 | 3/2006 | Bailey et al. | |
| 7,022,334 B1 | 4/2006 | Ding et al. | |
| 7,041,130 B2 | 5/2006 | Santini, Jr. | |
| 7,048,767 B2 | 5/2006 | Namavar | |
| 7,048,939 B2 | 5/2006 | Elkins et al. | |
| 7,052,488 B2 | 5/2006 | Uhland | |
| 7,056,338 B2 | 6/2006 | Shanley et al. | |
| 7,056,339 B2 | 6/2006 | Elkins et al. | |
| 7,060,051 B2 | 6/2006 | Palasis | |
| 7,060,240 B2 | 6/2006 | Costa et al. | |
| 7,063,748 B2 | 6/2006 | Talton | |
| 7,067,606 B2 | 6/2006 | Mather et al. | |
| 7,070,576 B2 | 7/2006 | O'Brien et al. | |
| 7,078,108 B2 | 7/2006 | Zhang et al. | |
| 7,099,091 B2 | 8/2006 | Taniguchi et al. | |
| 7,101,391 B2 | 9/2006 | Scheuermann et al. | |
| 7,101,394 B2 | 9/2006 | Hamm et al. | |
| 7,105,018 B1 | 9/2006 | Yip et al. | |
| 7,105,199 B2 | 9/2006 | Blinn et al. | |
| 7,108,716 B2 | 9/2006 | Burnside et al. | |
| 7,157,096 B2 | 1/2007 | Zhang et al. | |
| 7,160,592 B2 | 1/2007 | Rypacek et al. | |
| 7,163,715 B1 | 1/2007 | Kramer | |
| 7,169,173 B2 | 1/2007 | Hossainy et al. | |
| 7,169,178 B1 | 1/2007 | Santos et al. | |
| 7,195,640 B2 | 3/2007 | Falotico et al. | |
| 7,195,641 B2 | 3/2007 | Palmaz et al. | |
| 7,198,675 B2 | 4/2007 | Fox et al. | |
| 7,208,011 B2 | 4/2007 | Shanley et al. | |
| 7,208,172 B2 | 4/2007 | Birdsall et al. | |
| 7,220,816 B2 | 5/2007 | Pacetti | |
| 7,226,475 B2 | 6/2007 | Lenz et al. | |
| 7,229,471 B2 | 6/2007 | Gale et al. | |
| 7,235,096 B1 | 6/2007 | Van Tassel et al. | |
| 7,235,098 B2 | 6/2007 | Palmaz | |
| 7,238,199 B2 | 7/2007 | Feldman et al. | |
| 7,241,295 B2 | 7/2007 | Maguire | |
| 7,244,272 B2 | 7/2007 | Dubson et al. | |
| 7,261,732 B2 | 8/2007 | Justino | |
| 7,261,735 B2 | 8/2007 | Llanos et al. | |
| 7,267,960 B2 | 9/2007 | Galibert et al. | |
| 7,279,174 B2 | 10/2007 | Pacetti | |
| 7,279,175 B2 | 10/2007 | Chen | |
| 7,294,409 B2 | 11/2007 | Lye et al. | |
| 7,311,727 B2 | 12/2007 | Mazumder et al. | |
| 7,323,189 B2 | 1/2008 | Pathak | |
| RE40,122 E | 2/2008 | Thompson | |
| 7,331,993 B2 | 2/2008 | White | |
| 7,335,375 B2 | 2/2008 | Li et al. | |
| 7,344,560 B2 | 3/2008 | Gregorich et al. | |
| 7,344,563 B2 | 3/2008 | Vallana et al. | |
| 7,393,589 B2 | 7/2008 | Aharonov et al. | |
| 7,402,173 B2 | 7/2008 | Scheuermann et al. | |
| 7,416,558 B2 | 8/2008 | Yip et al. | |
| 7,432,327 B2 | 10/2008 | Glasgow et al. | |
| 7,462,366 B2 | 12/2008 | Lanphere | |
| 7,498,385 B2 | 3/2009 | Swetlin et al. | |
| 7,507,433 B2 | 3/2009 | Weber | |
| 7,537,610 B2 | 5/2009 | Reiss | |
| 7,547,445 B2 | 6/2009 | Chudzik et al. | |
| 7,563,277 B2 | 7/2009 | Case et al. | |
| 7,637,941 B1 | 12/2009 | Manicka et al. | |
| 7,651,527 B2 | 1/2010 | Krivoruchko et al. | |
| 7,691,401 B2 | 4/2010 | Castro et al. | |
| 7,713,297 B2 | 5/2010 | Alt | |
| 7,749,264 B2 | 7/2010 | Gregorich et al. | |
| 7,758,635 B2 | 7/2010 | Parsonage | |
| 7,771,773 B2 | 8/2010 | Namavar | |
| 7,776,926 B1 | 8/2010 | Claude et al. | |
| 2001/0001834 A1 | 5/2001 | Palmaz et al. | |
| 2001/0002000 A1 | 5/2001 | Kumar et al. | |
| 2001/0002435 A1 | 5/2001 | Berg et al. | |
| 2001/0013166 A1 | 8/2001 | Yan | |
| 2001/0021871 A1 | 9/2001 | Stinson | |
| 2001/0021873 A1 | 9/2001 | Stinson | |
| 2001/0027299 A1 | 10/2001 | Yang et al. | |
| 2001/0029398 A1 | 10/2001 | Jadhav ............... 623/1.22 | |
| 2001/0029660 A1 | 10/2001 | Johnson | |
| 2001/0032011 A1 | 10/2001 | Stanford | |
| 2001/0032013 A1 | 10/2001 | Marton | |
| 2001/0032014 A1 | 10/2001 | Yang et al. | |
| 2001/0044650 A1 | 11/2001 | Simso et al. | |
| 2002/0000175 A1 | 1/2002 | Hintermaier et al. | |
| 2002/0000406 A1 | 1/2002 | Izumi | |
| 2002/0004060 A1 | 1/2002 | Heublein et al. | |
| 2002/0007102 A1 | 1/2002 | Salmon et al. | |
| 2002/0007209 A1 | 1/2002 | Schearder et al. | |
| 2002/0010505 A1 | 1/2002 | Richter | |
| 2002/0016623 A1 | 2/2002 | Kula et al. | |
| 2002/0016624 A1 | 2/2002 | Patterson et al. | |
| 2002/0028827 A1 | 3/2002 | Naicker et al. | |
| 2002/0032477 A1 | 3/2002 | Helmus et al. | |
| 2002/0035394 A1 | 3/2002 | Fierens et al. | |
| 2002/0038146 A1 | 3/2002 | Harry | |
| 2002/0042039 A1 | 4/2002 | Kim et al. | |
| 2002/0049495 A1 | 4/2002 | Kutryk et al. | |
| 2002/0051730 A1 | 5/2002 | Bodnar et al. | |
| 2002/0051846 A1 | 5/2002 | Kirkpatrick et al. | |
| 2002/0065553 A1 | 5/2002 | Weber | |
| 2002/0082679 A1 | 6/2002 | Sirhan et al. | |
| 2002/0087123 A1 | 7/2002 | Hossainy et al. | |
| 2002/0090313 A1 | 7/2002 | Wang et al. | |
| 2002/0091375 A1 | 7/2002 | Sahatjian et al. | |
| 2002/0098278 A1 | 7/2002 | Bates et al. | |
| 2002/0099434 A1 | 7/2002 | Buscemi et al. | |
| 2002/0099438 A1 | 7/2002 | Furst | |
| 2002/0103527 A1 | 8/2002 | Kocur et al. | |
| 2002/0103528 A1 | 8/2002 | Schaldach et al. | |
| 2002/0111694 A1 | 8/2002 | Ellingsen et al. | |
| 2002/0121497 A1 | 9/2002 | Tomonto | |
| 2002/0123801 A1 | 9/2002 | Pacetti et al. | |
| 2002/0133222 A1 | 9/2002 | Das | |
| 2002/0133224 A1 | 9/2002 | Bajgar et al. | |
| 2002/0138100 A1 | 9/2002 | Stoll et al. | |
| 2002/0138131 A1 | 9/2002 | Solovay et al. | |
| 2002/0138136 A1 | 9/2002 | Chandresekaran et al. | |
| 2002/0138154 A1 | 9/2002 | Li et al. | |
| 2002/0144757 A1 | 10/2002 | Craig et al. | |
| 2002/0151964 A1 | 10/2002 | Smith et al. | |
| 2002/0155212 A1 | 10/2002 | Hossainy | |
| 2002/0165265 A1 | 11/2002 | Hunter et al. | |
| 2002/0165578 A1 | 11/2002 | Sawitowski et al. | |
| 2002/0165600 A1 | 11/2002 | Banas et al. | |
| 2002/0165607 A1 | 11/2002 | Alt | |
| 2002/0169493 A1 | 11/2002 | Widenhouse et al. | |
| 2002/0178570 A1 | 12/2002 | Sogard et al. | |
| 2002/0182241 A1 | 12/2002 | Borenstein et al. | |
| 2002/0183581 A1 | 12/2002 | Yoe et al. | |
| 2002/0187260 A1 | 12/2002 | Sheppard, Jr. et al. | |
| 2002/0193336 A1 | 12/2002 | Elkins et al. | |
| 2002/0193682 A1 | 12/2002 | Torchia et al. | |
| 2002/0193869 A1 | 12/2002 | Dang | |
| 2002/0197178 A1 | 12/2002 | Yan | |
| 2002/0198601 A1 | 12/2002 | Bales et al. | |
| 2003/0003127 A1 | 1/2003 | Brown et al. | |
| 2003/0003220 A1 | 1/2003 | Zhong et al. | |
| 2003/0004563 A1 | 1/2003 | Jackson et al. | |
| 2003/0004564 A1 | 1/2003 | Elkins et al. | |
| 2003/0009214 A1 | 1/2003 | Shanley | |
| 2003/0018380 A1 | 1/2003 | Craig et al. | |
| 2003/0018381 A1 | 1/2003 | Whitcher et al. | |
| 2003/0023300 A1 | 1/2003 | Bailey et al. | |
| 2003/0028242 A1 | 2/2003 | Vallana et al. | |
| 2003/0028243 A1 | 2/2003 | Bates et al. | |
| 2003/0032892 A1 | 2/2003 | Erlach et al. | |
| 2003/0033007 A1 | 2/2003 | Sirhan et al. | |
| 2003/0044446 A1 | 3/2003 | Moro et al. | |
| 2003/0050687 A1 | 3/2003 | Schwade et al. | |
| 2003/0059640 A1 | 3/2003 | Marton et al. | |
| 2003/0060871 A1 | 3/2003 | Hill et al. | |
| 2003/0060873 A1 | 3/2003 | Gertner et al. | |
| 2003/0064095 A1 | 4/2003 | Martin et al. | |
| 2003/0068355 A1 | 4/2003 | Shanley et al. | |

| | | | | | | |
|---|---|---|---|---|---|---|
| 2003/0069631 A1 | 4/2003 | Stoll | | 2004/0106985 A1 | 6/2004 | Jang |
| 2003/0074053 A1 | 4/2003 | Palmaz et al. | | 2004/0111150 A1 | 6/2004 | Berg et al. |
| 2003/0077200 A1 | 4/2003 | Craig et al. | | 2004/0116999 A1 | 6/2004 | Ledergerber |
| 2003/0077310 A1 | 4/2003 | Pathak et al. | | 2004/0117005 A1 | 6/2004 | Gadde et al. |
| 2003/0083614 A1 | 5/2003 | Eisert | | 2004/0117008 A1 | 6/2004 | Wnendt et al. |
| 2003/0083646 A1 | 5/2003 | Sirhan et al. | | 2004/0122504 A1 | 6/2004 | Hogendijk |
| 2003/0083731 A1 | 5/2003 | Kramer et al. | | 2004/0126566 A1 | 7/2004 | Axen et al. |
| 2003/0087024 A1 | 5/2003 | Flanagan | | 2004/0133270 A1 | 7/2004 | Grandt |
| 2003/0088307 A1 | 5/2003 | Shulze et al. | | 2004/0134886 A1 | 7/2004 | Wagner et al. |
| 2003/0088312 A1 | 5/2003 | Kopia et al. | | 2004/0137039 A1 | 7/2004 | Sukhishvili et al. |
| 2003/0099684 A1 | 5/2003 | Domb | | 2004/0138738 A1 | 7/2004 | Stinson |
| 2003/0100815 A1 | 5/2003 | Da Silva et al. | | 2004/0142014 A1 | 7/2004 | Litvack et al. |
| 2003/0100830 A1 | 5/2003 | Zhong et al. | | 2004/0143317 A1 | 7/2004 | Stinson et al. |
| 2003/0104030 A1 | 6/2003 | Igaki et al. | | 2004/0143321 A1 | 7/2004 | Litvack et al. |
| 2003/0105511 A1 | 6/2003 | Welsh et al. | | 2004/0148010 A1 | 7/2004 | Rush |
| 2003/0108659 A1 | 6/2003 | Bales et al. | | 2004/0148015 A1 | 7/2004 | Lye et al. |
| 2003/0114917 A1 | 6/2003 | Holloway et al. | | 2004/0153138 A1 | 8/2004 | Murphy |
| 2003/0114921 A1 | 6/2003 | Yoon | | 2004/0157073 A1 | 8/2004 | Burrell et al. |
| 2003/0118692 A1 | 6/2003 | Wang et al. | | 2004/0158308 A1 | 8/2004 | Hogendijk et al. |
| 2003/0120339 A1 | 6/2003 | Banik et al. | | 2004/0158310 A1 | 8/2004 | Weber et al. |
| 2003/0124055 A1 | 7/2003 | Li et al. | | 2004/0167572 A1 | 8/2004 | Roth et al. |
| 2003/0125803 A1 | 7/2003 | Vallana | | 2004/0167609 A1 | 8/2004 | Majercak |
| 2003/0130718 A1 | 7/2003 | Palmas et al. | | 2004/0167612 A1 | 8/2004 | Grignani et al. |
| 2003/0139799 A1 | 7/2003 | Ley et al. | | 2004/0172124 A1 | 9/2004 | Vallana et al. |
| 2003/0143330 A1 | 7/2003 | Loomis et al. | | 2004/0181252 A1 | 9/2004 | Boyle et al. |
| 2003/0144728 A1 | 7/2003 | Scheuermann et al. | | 2004/0181275 A1 | 9/2004 | Noble et al. |
| 2003/0150380 A1 | 8/2003 | Yoe | | 2004/0181276 A1 | 9/2004 | Brown et al. |
| 2003/0153901 A1 | 8/2003 | Herweck et al. | | 2004/0181278 A1 | 9/2004 | Tseng et al. |
| 2003/0158598 A1 | 8/2003 | Ashton et al. | | 2004/0182511 A1 | 9/2004 | Rakos et al. |
| 2003/0170605 A1 | 9/2003 | Long et al. | | 2004/0186553 A1 | 9/2004 | Yan |
| 2003/0181975 A1 | 9/2003 | Ishii et al. | | 2004/0191293 A1 | 9/2004 | Claude |
| 2003/0185895 A1 | 10/2003 | Lanphere | | 2004/0191404 A1 | 9/2004 | Hossainy et al. |
| 2003/0190406 A1 | 10/2003 | Hossainy et al. | | 2004/0202692 A1 | 10/2004 | Shanley et al. |
| 2003/0195613 A1 | 10/2003 | Curcio et al. | | 2004/0204750 A1 | 10/2004 | Dinh |
| 2003/0199993 A1 | 10/2003 | Gellman et al. | | 2004/0211362 A1 | 10/2004 | Castro et al. |
| 2003/0204239 A1 | 10/2003 | Carlyle et al. | | 2004/0219214 A1 | 11/2004 | Gravett et al. |
| 2003/0211135 A1 | 11/2003 | Greenhalgh et al. | | 2004/0220510 A1 | 11/2004 | Koullick et al. |
| 2003/0216803 A1 | 11/2003 | Ledergerber | | 2004/0220659 A1 | 11/2004 | Girton |
| 2003/0219562 A1 | 11/2003 | Rypacek et al. | | 2004/0220660 A1* | 11/2004 | Shanley et al. ............... 623/1.16 |
| 2003/0221307 A1 | 12/2003 | Kaese et al. | | 2004/0224001 A1 | 11/2004 | Pacetti et al. |
| 2003/0228523 A1 | 12/2003 | DeLongchamp et al. | | 2004/0225346 A1 | 11/2004 | Mazumder et al. |
| 2003/0236513 A1 | 12/2003 | Schwarz et al. | | 2004/0228905 A1 | 11/2004 | Greenspan et al. |
| 2004/0000046 A1 | 1/2004 | Stinson | | 2004/0230176 A1 | 11/2004 | Shanahan et al. |
| 2004/0000540 A1 | 1/2004 | Soboyejo et al. | | 2004/0230225 A1 | 11/2004 | Penner et al. |
| 2004/0004063 A1* | 1/2004 | Merdan .................... 219/121.67 | | 2004/0230290 A1 | 11/2004 | Weber et al. |
| 2004/0006382 A1 | 1/2004 | Sohier | | 2004/0230293 A1 | 11/2004 | Yip et al. |
| 2004/0018296 A1 | 1/2004 | Castro et al. | | 2004/0234737 A1 | 11/2004 | Pacetti |
| 2004/0019376 A1 | 1/2004 | Alt | | 2004/0236415 A1 | 11/2004 | Thomas |
| 2004/0022939 A1 | 2/2004 | Kim et al. | | 2004/0236416 A1 | 11/2004 | Falotico |
| 2004/0024448 A1 | 2/2004 | Chang et al. | | 2004/0237282 A1 | 12/2004 | Hines |
| 2004/0029303 A1 | 2/2004 | Hart et al. | | 2004/0242106 A1 | 12/2004 | Rabasco et al. |
| 2004/0030218 A1 | 2/2004 | Kocur et al. | | 2004/0243217 A1 | 12/2004 | Andersen |
| 2004/0030377 A1 | 2/2004 | Dubson et al. | | 2004/0243237 A1 | 12/2004 | Unwin et al. |
| 2004/0034409 A1 | 2/2004 | Heublein et al. | | 2004/0243241 A1 | 12/2004 | Istephanous et al. |
| 2004/0039438 A1 | 2/2004 | Alt et al. | | 2004/0247671 A1 | 12/2004 | Prescott et al. |
| 2004/0039441 A1 | 2/2004 | Rowland et al. | | 2004/0249440 A1 | 12/2004 | Bucker et al. |
| 2004/0044397 A1 | 3/2004 | Stinson | | 2004/0249443 A1 | 12/2004 | Shanley et al. |
| 2004/0047980 A1 | 3/2004 | Pacetti et al. | | 2004/0249444 A1 | 12/2004 | Reiss |
| 2004/0059407 A1 | 3/2004 | Escamilla et al. | | 2004/0249445 A1 | 12/2004 | Rosenthal et al. |
| 2004/0059409 A1 | 3/2004 | Stenzel | | 2004/0249449 A1 | 12/2004 | Shanley et al. |
| 2004/0067301 A1 | 4/2004 | Ding | | 2004/0254419 A1 | 12/2004 | Wang et al. |
| 2004/0071861 A1 | 4/2004 | Mandrusov et al. | | 2004/0254635 A1 | 12/2004 | Shanley et al. |
| 2004/0073155 A1 | 4/2004 | Laufer et al. | | 2005/0004661 A1 | 1/2005 | Lewis et al. |
| 2004/0073284 A1 | 4/2004 | Bates et al. | | 2005/0010275 A1 | 1/2005 | Sahatjian |
| 2004/0073293 A1 | 4/2004 | Thompson | | 2005/0010279 A1 | 1/2005 | Tenerz et al. |
| 2004/0073297 A1 | 4/2004 | Rohde et al. | | 2005/0015142 A1 | 1/2005 | Austin et al. |
| 2004/0073298 A1 | 4/2004 | Hossainy | | 2005/0019265 A1 | 1/2005 | Hammer et al. |
| 2004/0078071 A1 | 4/2004 | Escamilla et al. | | 2005/0019371 A1 | 1/2005 | Anderson et al. |
| 2004/0082682 A1 | 4/2004 | Loomis et al. | | 2005/0021127 A1 | 1/2005 | Kawula |
| 2004/0088038 A1 | 5/2004 | Dehnad et al. | | 2005/0021128 A1 | 1/2005 | Nakahama et al. |
| 2004/0088041 A1 | 5/2004 | Stanford | | 2005/0022627 A1 | 2/2005 | Chen |
| 2004/0093071 A1 | 5/2004 | Jang | | 2005/0025804 A1 | 2/2005 | Heller |
| 2004/0093075 A1 | 5/2004 | Kuehne | | 2005/0027350 A1 | 2/2005 | Momma et al. |
| 2004/0093076 A1 | 5/2004 | White et al. | | 2005/0033407 A1 | 2/2005 | Weber et al. |
| 2004/0098089 A1 | 5/2004 | Weber | | 2005/0033411 A1 | 2/2005 | Wu et al. |
| 2004/0098108 A1 | 5/2004 | Harder et al. ................. 623/1.15 | | 2005/0033412 A1 | 2/2005 | Wu et al. |
| 2004/0098119 A1 | 5/2004 | Wang | | 2005/0033417 A1 | 2/2005 | Borges et al. |
| 2004/0106975 A1 | 6/2004 | Solovay et al. | | 2005/0037047 A1 | 2/2005 | Song |
| 2004/0106984 A1 | 6/2004 | Stinson | | 2005/0037050 A1 | 2/2005 | Weber |

| | | | | | | |
|---|---|---|---|---|---|---|
| 2005/0038134 A1 | 2/2005 | Loomis et al. | | 2005/0221072 A1 | 10/2005 | Dubrow et al. |
| 2005/0038501 A1 | 2/2005 | Moore, Jr. et al. | | 2005/0222671 A1 | 10/2005 | Schaeffer et al. |
| 2005/0042288 A1 | 2/2005 | Koblish et al. | | 2005/0228477 A1 | 10/2005 | Grainger et al. |
| 2005/0042440 A1 | 2/2005 | Bach et al. | | 2005/0228483 A1 | 10/2005 | Kaplan et al. |
| 2005/0055044 A1 | 3/2005 | Kangas | | 2005/0228491 A1 | 10/2005 | Snyder et al. |
| 2005/0055080 A1 | 3/2005 | Istephanous et al. | | 2005/0232968 A1 | 10/2005 | Palmaz et al. |
| 2005/0055085 A1 | 3/2005 | Rivron et al. | | 2005/0233965 A1 | 10/2005 | Schwartz et al. |
| 2005/0060020 A1 | 3/2005 | Jenson | | 2005/0234538 A1 | 10/2005 | Litvack et al. |
| 2005/0060021 A1 | 3/2005 | O'Brien et al. | | 2005/0240280 A1 | 10/2005 | Aliski et al. |
| 2005/0064088 A1 | 3/2005 | Fredrickson | | 2005/0244459 A1 | 11/2005 | DeWitt et al. |
| 2005/0069630 A1 | 3/2005 | Fox et al. | | 2005/0251245 A1 | 11/2005 | Sieradzki et al. |
| 2005/0070989 A1 | 3/2005 | Lye et al. | | 2005/0251249 A1 | 11/2005 | Sahatjian |
| 2005/0070990 A1 | 3/2005 | Stinson | | 2005/0252893 A1 | 11/2005 | Shapovalov et al. ..... 219/121.72 |
| 2005/0070996 A1 | 3/2005 | Dinh et al. | | 2005/0255707 A1 | 11/2005 | Hart et al. |
| 2005/0071016 A1 | 3/2005 | Hausdorf et al. | | 2005/0261760 A1 | 11/2005 | Weber ......................... 623/1.38 |
| 2005/0072544 A1 | 4/2005 | Palmaz et al. | | 2005/0266039 A1 | 12/2005 | Weber |
| 2005/0074479 A1 | 4/2005 | Weber et al. | | 2005/0266040 A1 | 12/2005 | Gerberding |
| 2005/0074545 A1 | 4/2005 | Thomas | | 2005/0266041 A1 | 12/2005 | Gerold et al. |
| 2005/0075714 A1 | 4/2005 | Cheng et al. | | 2005/0267560 A1 | 12/2005 | Bates ............................. 623/1.1 |
| 2005/0077305 A1 | 4/2005 | Guevara | | 2005/0267561 A1 | 12/2005 | Jones et al. |
| 2005/0079132 A1 | 4/2005 | Wang et al. | | 2005/0271703 A1 | 12/2005 | Anderson et al. |
| 2005/0079199 A1 | 4/2005 | Heruth et al. | | 2005/0271706 A1 | 12/2005 | Anderson et al. |
| 2005/0079356 A1 | 4/2005 | Rathenow et al. | | 2005/0276837 A1 | 12/2005 | Anderson et al. |
| 2005/0092615 A1 | 5/2005 | Birdsall et al. | | 2005/0278016 A1 | 12/2005 | Welsh et al. |
| 2005/0096731 A1 | 5/2005 | Looi et al. | | 2005/0278021 A1 | 12/2005 | Bates et al. |
| 2005/0100577 A1 | 5/2005 | Parker et al. | | 2005/0281863 A1 | 12/2005 | Anderson et al. |
| 2005/0100609 A1 | 5/2005 | Claude | | 2005/0283224 A1 | 12/2005 | King |
| 2005/0102025 A1 | 5/2005 | Laroche et al. | | 2005/0283229 A1 | 12/2005 | Dugan et al. |
| 2005/0106212 A1 | 5/2005 | Gertner et al. | | 2005/0287188 A1 | 12/2005 | Anderson et al. |
| 2005/0107869 A1 | 5/2005 | Sirhan et al. | | 2006/0002979 A1 | 1/2006 | Ashammakhi et al. |
| 2005/0107870 A1 | 5/2005 | Wang et al. | | 2006/0009839 A1 | 1/2006 | Tan |
| 2005/0113936 A1 | 5/2005 | Brustad et al. | | 2006/0013850 A1 | 1/2006 | Domb |
| 2005/0119723 A1 | 6/2005 | Peacock | | 2006/0014039 A1 | 1/2006 | Zhang et al. |
| 2005/0129727 A1 | 6/2005 | Weber et al. | | 2006/0015175 A1 | 1/2006 | Palmaz et al. |
| 2005/0129731 A1 | 6/2005 | Horres et al. | | 2006/0015361 A1 | 1/2006 | Sattler et al. |
| 2005/0131509 A1 | 6/2005 | Atanasoska et al. | | 2006/0020742 A1 | 1/2006 | Au et al. |
| 2005/0131521 A1 | 6/2005 | Marton | | 2006/0025848 A1 | 2/2006 | Weber et al. |
| 2005/0131522 A1 | 6/2005 | Stinson et al. | | 2006/0035026 A1 | 2/2006 | Atanasoska et al. |
| 2005/0131527 A1 | 6/2005 | Pathak | | 2006/0036281 A1 | 2/2006 | Patterson et al. |
| 2005/0131528 A1 | 6/2005 | Buscemi et al. | | 2006/0036311 A1 | 2/2006 | Nakayama et al. |
| 2005/0136090 A1 | 6/2005 | Falotico et al. | | 2006/0038027 A1 | 2/2006 | O'Connor et al. |
| 2005/0137677 A1 | 6/2005 | Rush | | 2006/0040388 A1 | 2/2006 | Bromberg et al. |
| 2005/0137679 A1 | 6/2005 | Changelian et al. | | 2006/0041182 A1 | 2/2006 | Forbes et al. |
| 2005/0137684 A1 | 6/2005 | Changelian et al. | | 2006/0051397 A1 | 3/2006 | Maier et al. |
| 2005/0149169 A1 | 7/2005 | Wang et al. | | 2006/0052744 A1 | 3/2006 | Weber |
| 2005/0149170 A1 | 7/2005 | Tassel et al. | | 2006/0052863 A1 | 3/2006 | Harder et al. |
| 2005/0149175 A1 | 7/2005 | Hunter et al. | | 2006/0052864 A1 | 3/2006 | Harder et al. |
| 2005/0149177 A1 | 7/2005 | Weber et al. | | 2006/0058868 A1 | 3/2006 | Gale et al. |
| 2005/0159804 A1 | 7/2005 | Lad et al. | | 2006/0062820 A1 | 3/2006 | Gertner et al. |
| 2005/0159805 A1 | 7/2005 | Weber et al. | | 2006/0064160 A1 | 3/2006 | Gerold et al. |
| 2005/0159809 A1 | 7/2005 | Hezi-Yamit et al. | | 2006/0067908 A1 | 3/2006 | Ding |
| 2005/0160600 A1 | 7/2005 | Bien et al. | | 2006/0069427 A1 | 3/2006 | Savage et al. |
| 2005/0163821 A1 | 7/2005 | Sung et al. | | 2006/0075044 A1 | 4/2006 | Fox et al. |
| 2005/0163954 A1 | 7/2005 | Shaw | | 2006/0075092 A1 | 4/2006 | Kidokoro |
| 2005/0165301 A1 | 7/2005 | Smith et al. | | 2006/0079958 A1 | 4/2006 | Stratford et al. |
| 2005/0165468 A1 | 7/2005 | Marton | | 2006/0085062 A1 | 4/2006 | Lee et al. |
| 2005/0165470 A1 | 7/2005 | Weber | | 2006/0085065 A1 | 4/2006 | Krause et al. |
| 2005/0169969 A1 | 8/2005 | Li et al. | | 2006/0088566 A1 | 4/2006 | Parsonage et al. |
| 2005/0171595 A1 | 8/2005 | Feldman et al. | | 2006/0088567 A1 | 4/2006 | Warner et al. |
| 2005/0177226 A1 | 8/2005 | Banik et al. | | 2006/0088653 A1 | 4/2006 | Chappa et al. |
| 2005/0180919 A1 | 8/2005 | Tedeschi | | 2006/0088666 A1 | 4/2006 | Kobrin et al. |
| 2005/0182361 A1 | 8/2005 | Lennox | | 2006/0100696 A1 | 5/2006 | Atanasoska et al. |
| 2005/0182478 A1 | 8/2005 | Holman et al. | | 2006/0115512 A1 | 6/2006 | Peacock et al. |
| 2005/0186250 A1 | 8/2005 | Gertner et al. | | 2006/0118236 A1 | 6/2006 | House et al. |
| 2005/0187605 A1 | 8/2005 | Greenhalgh et al. | | 2006/0121080 A1 | 6/2006 | Lye et al. |
| 2005/0187611 A1 | 8/2005 | Ding et al. | | 2006/0122694 A1 | 6/2006 | Stinson et al. |
| 2005/0192657 A1 | 9/2005 | Colen et al. | | 2006/0122697 A1 | 6/2006 | Shanley et al. |
| 2005/0192662 A1 | 9/2005 | Ward | | 2006/0124472 A1 | 6/2006 | Rokicki |
| 2005/0192664 A1 | 9/2005 | Eisert | | 2006/0127266 A1 | 6/2006 | Miura et al. |
| 2005/0196424 A1 | 9/2005 | Chappa | | 2006/0129215 A1 | 6/2006 | Helmus et al. |
| 2005/0208098 A1 | 9/2005 | Castro et al. | | 2006/0129222 A1 | 6/2006 | Stinson |
| 2005/0208100 A1 | 9/2005 | Weber et al. | | 2006/0129225 A1 | 6/2006 | Kopia et al. |
| 2005/0209680 A1 | 9/2005 | Gale et al. | | 2006/0136048 A1 | 6/2006 | Pacetti et al. |
| 2005/0209681 A1 | 9/2005 | Curcio et al. | | 2006/0136051 A1 | 6/2006 | Furst et al. |
| 2005/0211680 A1 | 9/2005 | Li et al. | | 2006/0141156 A1 | 6/2006 | Viel et al. |
| 2005/0214951 A1 | 9/2005 | Nahm et al. | | 2006/0149352 A1 | 7/2006 | Schlum |
| 2005/0216074 A1 | 9/2005 | Sahatjian | | 2006/0153729 A1 | 7/2006 | Stinson et al. |
| 2005/0216075 A1 | 9/2005 | Wang et al. | | 2006/0155361 A1 | 7/2006 | Schomig et al. |
| 2005/0220853 A1 | 10/2005 | Dao et al. | | 2006/0167543 A1 | 7/2006 | Bailey et al. |

| Publication No. | Date | Inventor |
|---|---|---|
| 2006/0177480 A1 | 8/2006 | Sung et al. |
| 2006/0178727 A1 | 8/2006 | Richter |
| 2006/0184235 A1 | 8/2006 | Rivron et al. |
| 2006/0193886 A1 | 8/2006 | Owens et al. |
| 2006/0193887 A1 | 8/2006 | Owens et al. |
| 2006/0193888 A1 | 8/2006 | Lye et al. |
| 2006/0193889 A1 | 8/2006 | Spradlin et al. |
| 2006/0193890 A1 | 8/2006 | Owens et al. |
| 2006/0193892 A1 | 8/2006 | Furst et al. |
| 2006/0195142 A1 | 8/2006 | Shalaby |
| 2006/0198869 A1 | 9/2006 | Furst et al. |
| 2006/0199876 A1 | 9/2006 | Troczynski et al. |
| 2006/0200229 A1 | 9/2006 | Burgermeister et al. |
| 2006/0200231 A1 | 9/2006 | O'Brien et al. |
| 2006/0200232 A1 | 9/2006 | Phaneuf et al. |
| 2006/0200233 A1 | 9/2006 | Kujawski |
| 2006/0204441 A1 | 9/2006 | Atala et al. |
| 2006/0204445 A1 | 9/2006 | Atala et al. |
| 2006/0210595 A1 | 9/2006 | Singhvi et al. |
| 2006/0212108 A1 | 9/2006 | Tittelbach |
| 2006/0022971 A1 | 10/2006 | Yan et al. |
| 2006/0222679 A1 | 10/2006 | Shanley et al. |
| 2006/0222844 A1 | 10/2006 | Stinson |
| 2006/0224237 A1 | 10/2006 | Furst et al. |
| 2006/0229711 A1 | 10/2006 | Yan et al. |
| 2006/0229713 A1 | 10/2006 | Shanley et al. |
| 2006/0230476 A1 | 10/2006 | Atanasoska et al. |
| 2006/0233941 A1 | 10/2006 | Olson |
| 2006/0241739 A1 | 10/2006 | Besselink et al. |
| 2006/0251701 A1 | 11/2006 | Lynn et al. |
| 2006/0259133 A1 | 11/2006 | Sowinski et al. |
| 2006/0264138 A1 | 11/2006 | Sowinski et al. |
| 2006/0271156 A1 | 11/2006 | Ledergerber |
| 2006/0271168 A1 | 11/2006 | Kleine et al. |
| 2006/0271169 A1 | 11/2006 | Lye et al. |
| 2006/0271192 A1 | 11/2006 | Olsen et al. |
| 2006/0271193 A1 | 11/2006 | Hartmann et al. |
| 2006/0275554 A1 | 12/2006 | Zhao et al. |
| 2006/0276877 A1 | 12/2006 | Owens et al. |
| 2006/0276878 A1 | 12/2006 | Owens et al. |
| 2006/0276879 A1 | 12/2006 | Lye et al. |
| 2006/0276884 A1 | 12/2006 | Lye et al. |
| 2006/0276885 A1 | 12/2006 | Lye et al. |
| 2006/0280770 A1 | 12/2006 | Hossainy et al. |
| 2006/0287709 A1 | 12/2006 | Rao |
| 2006/0292388 A1 | 12/2006 | Palumbo et al. |
| 2007/0003589 A1 | 1/2007 | Astafieva et al. |
| 2007/0003596 A1 | 1/2007 | Tittelbach et al. |
| 2007/0020306 A1 | 1/2007 | Schultheiss |
| 2007/0027532 A1 | 2/2007 | Wang et al. |
| 2007/0032858 A1 | 2/2007 | Santos et al. |
| 2007/0032862 A1 | 2/2007 | Weber et al. |
| 2007/0032864 A1 | 2/2007 | Furst et al. |
| 2007/0034615 A1 | 2/2007 | Kleine |
| 2007/0036905 A1 | 2/2007 | Kramer |
| 2007/0038176 A1 | 2/2007 | Weber et al. |
| 2007/0038289 A1 | 2/2007 | Nishide et al. |
| 2007/0038290 A1 | 2/2007 | Huang et al. |
| 2007/0045252 A1 | 3/2007 | Kleine et al. |
| 2007/0048350 A1 | 3/2007 | Faltico et al. |
| 2007/0050007 A1 | 3/2007 | Kondyurin et al. |
| 2007/0050009 A1 | 3/2007 | Flanagan |
| 2007/0052497 A1 | 3/2007 | Tada |
| 2007/0055349 A1 | 3/2007 | Santos et al. |
| 2007/0055354 A1 | 3/2007 | Santos et al. |
| 2007/0055364 A1 | 3/2007 | Hossainy et al. |
| 2007/0059435 A1 | 3/2007 | Santos et al. |
| 2007/0065418 A1 | 3/2007 | Vallana et al. |
| 2007/0073385 A1 | 3/2007 | Schaeffer et al. |
| 2007/0073390 A1 | 3/2007 | Lee |
| 2007/0077163 A1 | 4/2007 | Furst et al. |
| 2007/0100385 A1 | 5/2007 | Rawat et al. |
| 2007/0104753 A1 | 5/2007 | Flanagan |
| 2007/0106347 A1 | 5/2007 | Lin |
| 2007/0106363 A1 | 5/2007 | Weber |
| 2007/0123131 A1 | 5/2007 | Nguyen et al. |
| 2007/0123973 A1 | 5/2007 | Roth et al. |
| 2007/0129789 A1 | 6/2007 | Cottone, Jr. et al. |
| 2007/0129792 A1 | 6/2007 | Picart et al. |
| 2007/0134288 A1 | 6/2007 | Parsonage et al. |
| 2007/0135908 A1 | 6/2007 | Zhao |
| 2007/0141106 A1 | 6/2007 | Bonutti et al. |
| 2007/0142897 A1 | 6/2007 | Consigny et al. |
| 2007/0142899 A1 | 6/2007 | Lootz et al. |
| 2007/0148251 A1 | 6/2007 | Hossainy et al. |
| 2007/0151093 A1 | 7/2007 | Curcio et al. |
| 2007/0156231 A1 | 7/2007 | Weber |
| 2007/0156248 A1 | 7/2007 | Marco et al. |
| 2007/0160641 A1 | 7/2007 | Jang |
| 2007/0168016 A1 | 7/2007 | Gronemeyer et al. |
| 2007/0173923 A1 | 7/2007 | Savage et al. |
| 2007/0178129 A1 | 8/2007 | Flanagan |
| 2007/0181433 A1 | 8/2007 | Birdsall et al. |
| 2007/0184083 A1 | 8/2007 | Coughlin |
| 2007/0190104 A1 | 8/2007 | Kamath et al. |
| 2007/0191923 A1 | 8/2007 | Weber |
| 2007/0191928 A1 | 8/2007 | Rolando et al. |
| 2007/0191931 A1 | 8/2007 | Weber et al. |
| 2007/0191943 A1 | 8/2007 | Shrivastava et al. |
| 2007/0197980 A1 | 8/2007 | Barry et al. |
| 2007/0202466 A1 | 8/2007 | Schwarz et al. |
| 2007/0207186 A1 | 9/2007 | Scanlon et al. |
| 2007/0208412 A1 | 9/2007 | Elmaleh |
| 2007/0219626 A1 | 9/2007 | Rolando et al. |
| 2007/0224116 A1 | 9/2007 | Chandrasekaran et al. |
| 2007/0224244 A1 | 9/2007 | Weber et al. |
| 2007/0225799 A1 | 9/2007 | Doty |
| 2007/0244541 A1 | 10/2007 | Schulman |
| 2007/0244569 A1 | 10/2007 | Weber et al. |
| 2007/0250155 A1 | 10/2007 | Simpson |
| 2007/0250156 A1 | 10/2007 | Palmaz |
| 2007/0250158 A1 | 10/2007 | Krivoruchko et al. |
| 2007/0255388 A1 | 11/2007 | Rudakov et al. |
| 2007/0255392 A1 | 11/2007 | Johnson |
| 2007/0264199 A1 | 11/2007 | Labhasetwar et al. |
| 2007/0264303 A1 | 11/2007 | Atanasoska et al. |
| 2007/0270940 A1 | 11/2007 | Doty |
| 2007/0270942 A1 | 11/2007 | Thomas |
| 2007/0281073 A1 | 12/2007 | Gale et al. |
| 2007/0281117 A1 | 12/2007 | Kaplan et al. |
| 2007/0282432 A1 | 12/2007 | Stinson et al. |
| 2007/0299509 A1 | 12/2007 | Ding |
| 2007/0299512 A1 | 12/2007 | Korzuschnik et al. |
| 2008/0003251 A1 | 1/2008 | Zhou |
| 2008/0003256 A1 | 1/2008 | Martens et al. |
| 2008/0003431 A1 | 1/2008 | Fellinger et al. |
| 2008/0004691 A1 | 1/2008 | Weber et al. |
| 2008/0031765 A1 | 2/2008 | Gerold et al. |
| 2008/0033522 A1 | 2/2008 | Grewe et al. |
| 2008/0033530 A1 | 2/2008 | Zberg et al. |
| 2008/0033531 A1 | 2/2008 | Barthel et al. |
| 2008/0033533 A1 | 2/2008 | Borck |
| 2008/0033536 A1 | 2/2008 | Wittchow |
| 2008/0033537 A1 | 2/2008 | Tittelbach |
| 2008/0033538 A1 | 2/2008 | Borck et al. |
| 2008/0033539 A1 | 2/2008 | Sternberg et al. |
| 2008/0033576 A1 | 2/2008 | Gerold et al. |
| 2008/0038146 A1 | 2/2008 | Wachter et al. |
| 2008/0050413 A1 | 2/2008 | Horvers et al. |
| 2008/0051335 A1 | 2/2008 | Kleiner et al. |
| 2008/0051866 A1 | 2/2008 | Chen et al. |
| 2008/0051872 A1 | 2/2008 | Borck |
| 2008/0051881 A1 | 2/2008 | Feng et al. |
| 2008/0057105 A1 | 3/2008 | Atanasoska et al. |
| 2008/0058919 A1 | 3/2008 | Kramer-Brown et al. |
| 2008/0058921 A1 | 3/2008 | Lindquist |
| 2008/0058923 A1 | 3/2008 | Bertsch et al. |
| 2008/0069854 A1 | 3/2008 | Xiao et al. |
| 2008/0069858 A1 | 3/2008 | Weber |
| 2008/0071348 A1 | 3/2008 | Boismier et al. |
| 2008/0071349 A1 | 3/2008 | Atanasoska et al. |
| 2008/0071350 A1 | 3/2008 | Stinson |
| 2008/0071351 A1 | 3/2008 | Flanagan et al. |
| 2008/0071352 A1 | 3/2008 | Weber et al. |
| 2008/0071353 A1 | 3/2008 | Weber et al. |
| 2008/0071355 A1 | 3/2008 | Weber et al. |
| 2008/0071357 A1 | 3/2008 | Girton et al. |
| 2008/0071358 A1 | 3/2008 | Weber et al. |

| | | |
|---|---|---|
| 2008/0082162 A1 | 4/2008 | Boismier et al. |
| 2008/0086199 A1 | 4/2008 | Dave et al. |
| 2008/0086201 A1 | 4/2008 | Weber et al. |
| 2008/0090097 A1 | 4/2008 | Shaw et al. |
| 2008/0097577 A1 | 4/2008 | Atanasoska et al. |
| 2008/0103589 A1 | 5/2008 | Cheng et al. |
| 2008/0103594 A1 | 5/2008 | Loffler et al. |
| 2008/0107890 A1 | 5/2008 | Bureau et al. |
| 2008/0109072 A1 | 5/2008 | Girton |
| 2008/0113083 A1 | 5/2008 | Sutermeister et al. |
| 2008/0124373 A1 | 5/2008 | Xiao et al. |
| 2008/0131479 A1 | 6/2008 | Weber et al. |
| 2008/0140172 A1 | 6/2008 | Carpenter et al. |
| 2008/0140186 A1 | 6/2008 | Grignani et al. |
| 2008/0145400 A1 | 6/2008 | Weber et al. |
| 2008/0147175 A1 | 6/2008 | Krivoruchko et al. |
| 2008/0147177 A1 | 6/2008 | Scheuermann et al. |
| 2008/0148002 A1 | 6/2008 | Fleming |
| 2008/0152929 A1 | 6/2008 | Zhao |
| 2008/0160166 A1 | 7/2008 | Rypacek et al. |
| 2008/0160259 A1 | 7/2008 | Nielson et al. |
| 2008/0161906 A1 | 7/2008 | Atanasoska et al. |
| 2008/0171929 A1 | 7/2008 | Katims |
| 2008/0175885 A1 | 7/2008 | Asgari |
| 2008/0177378 A1 | 7/2008 | Asgari |
| 2008/0183269 A2 | 7/2008 | Kaplan et al. |
| 2008/0183277 A1 | 7/2008 | Atanasoska et al. |
| 2008/0183278 A1 | 7/2008 | Atanasoska et al. |
| 2008/0188927 A1 | 8/2008 | Rohde et al. |
| 2008/0195170 A1 | 8/2008 | Asgari |
| 2008/0195189 A1 | 8/2008 | Asgari |
| 2008/0195198 A1 | 8/2008 | Asgari |
| 2008/0208308 A1 | 8/2008 | Allen et al. |
| 2008/0208313 A1 | 8/2008 | Yu et al. |
| 2008/0208352 A1 | 8/2008 | Krivoruchko et al. |
| 2008/0213377 A1 | 9/2008 | Bhatia et al. |
| 2008/0215129 A1 | 9/2008 | Venturelli et al. |
| 2008/0215139 A1 | 9/2008 | McMorrow et al. |
| 2008/0215140 A1 | 9/2008 | Borck et al. |
| 2008/0241218 A1 | 10/2008 | McMorrow et al. |
| 2008/0243113 A1 | 10/2008 | Shastri et al. |
| 2008/0243230 A1 | 10/2008 | Lootz et al. |
| 2008/0243231 A1 | 10/2008 | Flanagan et al. |
| 2008/0243234 A1 | 10/2008 | Wilcox |
| 2008/0243240 A1 | 10/2008 | Doty et al. |
| 2008/0243242 A1 | 10/2008 | Kappelt et al. |
| 2008/0249600 A1 | 10/2008 | Atanasoska et al. |
| 2008/0249615 A1 | 10/2008 | Weber |
| 2008/0255508 A1 | 10/2008 | Wang |
| 2008/0255509 A1 | 10/2008 | Wang |
| 2008/0262589 A1 | 10/2008 | Nagura |
| 2008/0268308 A1* | 10/2008 | Schilling et al. ............... 429/20 |
| 2008/0269872 A1 | 10/2008 | Lootz et al. |
| 2008/0288048 A1 | 11/2008 | Rolando et al. |
| 2008/0290467 A1 | 11/2008 | Shue |
| 2008/0294236 A1 | 11/2008 | Anand et al. |
| 2008/0294246 A1 | 11/2008 | Scheuermann |
| 2008/0306584 A1 | 12/2008 | Kramer-Brown |
| 2009/0005862 A1 | 1/2009 | Nakatani et al. |
| 2009/0012599 A1 | 1/2009 | Broome et al. |
| 2009/0018639 A1 | 1/2009 | Kuehling |
| 2009/0018647 A1 | 1/2009 | Benco et al. |
| 2009/0018648 A1 | 1/2009 | Wittchow |
| 2009/0022771 A1 | 1/2009 | Lynn et al. |
| 2009/0024199 A1 | 1/2009 | Birdsall et al. |
| 2009/0024209 A1 | 1/2009 | Ozdil et al. |
| 2009/0024210 A1 | 1/2009 | Klocke et al. |
| 2009/0024211 A1 | 1/2009 | Wittchow |
| 2009/0028785 A1 | 1/2009 | Clarke |
| 2009/0030494 A1 | 1/2009 | Stefanadis et al. |
| 2009/0030500 A1 | 1/2009 | Weber et al. |
| 2009/0030504 A1 | 1/2009 | Weber et al. |
| 2009/0030506 A1 | 1/2009 | Klocke et al. |
| 2009/0030507 A1 | 1/2009 | Klocke et al. |
| 2009/0035351 A1 | 2/2009 | Berglund et al. |
| 2009/0043330 A1 | 2/2009 | To |
| 2009/0043374 A1 | 2/2009 | Nakano |
| 2009/0043380 A1 | 2/2009 | Blaha et al. |
| 2009/0048660 A1 | 2/2009 | Adden |
| 2009/0062905 A1 | 3/2009 | Moore, Jr. et al. |
| 2009/0069884 A1 | 3/2009 | Mueller |
| 2009/0076588 A1 | 3/2009 | Weber |
| 2009/0076596 A1 | 3/2009 | Adden et al. |
| 2009/0081293 A1 | 3/2009 | Murase et al. |
| 2009/0081450 A1 | 3/2009 | Ascher et al. |
| 2009/0088831 A1 | 4/2009 | Goto |
| 2009/0088834 A1 | 4/2009 | Wang |
| 2009/0093871 A1 | 4/2009 | Rea et al. |
| 2009/0095715 A1 | 4/2009 | Sabaria |
| 2009/0118809 A1 | 5/2009 | Scheuermann et al. |
| 2009/0118812 A1 | 5/2009 | Kokate et al. |
| 2009/0118813 A1 | 5/2009 | Scheuermann et al. |
| 2009/0118814 A1 | 5/2009 | Schoenle et al. |
| 2009/0118815 A1 | 5/2009 | Arcand et al. |
| 2009/0118818 A1 | 5/2009 | Foss et al. |
| 2009/0118819 A1 | 5/2009 | Merz et al. |
| 2009/0118820 A1 | 5/2009 | Gregorich et al. |
| 2009/0118821 A1 | 5/2009 | Scheuermann et al. |
| 2009/0118822 A1 | 5/2009 | Holman et al. |
| 2009/0118823 A1 | 5/2009 | Atanasoska et al. |
| 2009/0123517 A1 | 5/2009 | Flanagan et al. |
| 2009/0123521 A1 | 5/2009 | Weber et al. |
| 2009/0124956 A1 | 5/2009 | Swetlin et al. |
| 2009/0131540 A1 | 5/2009 | Hiromoto et al. |
| 2009/0143855 A1 | 6/2009 | Weber et al. |
| 2009/0149942 A1 | 6/2009 | Edelman et al. |
| 2009/0157165 A1 | 6/2009 | Miller et al. |
| 2009/0157172 A1 | 6/2009 | Kokate et al. |
| 2009/0164002 A1 | 6/2009 | Becher et al. |
| 2009/0171452 A1 | 7/2009 | Yamamoto et al. |
| 2009/0177273 A1 | 7/2009 | Piveteau et al. |
| 2009/0182290 A1 | 7/2009 | Harder et al. |
| 2009/0182337 A1 | 7/2009 | Stopek et al. |
| 2009/0182425 A1 | 7/2009 | Duda et al. |
| 2009/0192571 A1 | 7/2009 | Stett et al. |
| 2009/0192594 A1 | 7/2009 | Borck |
| 2009/0192595 A1 | 7/2009 | Nagura et al. |
| 2009/0192596 A1 | 7/2009 | Adden |
| 2009/0196899 A1 | 8/2009 | Birdsall et al. |
| 2009/0198320 A1 | 8/2009 | Mueller et al. |
| 2009/0202610 A1 | 8/2009 | Wilson |
| 2009/0204203 A1 | 8/2009 | Allen et al. |
| 2009/0208428 A1 | 8/2009 | Hill et al. |
| 2009/0208555 A1 | 8/2009 | Kuttler et al. |
| 2009/0214373 A1 | 8/2009 | Stinson et al. |
| 2009/0220612 A1 | 9/2009 | Perera |
| 2009/0228037 A1 | 9/2009 | Rego |
| 2009/0240323 A1 | 9/2009 | Wilcox |
| 2009/0254171 A1 | 10/2009 | Heikkila |
| 2009/0259300 A1 | 10/2009 | Dorogy, Jr. et al. |
| 2009/0270979 A1 | 10/2009 | Adden |
| 2009/0274737 A1 | 11/2009 | Borck |
| 2009/0281613 A1 | 11/2009 | Atanasoska et al. |
| 2009/0287301 A1 | 11/2009 | Weber |
| 2009/0287302 A1 | 11/2009 | Thomas et al. |
| 2009/0306584 A1 | 12/2009 | Schmidtlein et al. |
| 2009/0306756 A1 | 12/2009 | Cho et al. |
| 2009/0306765 A1 | 12/2009 | Weber |
| 2009/0306766 A1 | 12/2009 | McDermott et al. |
| 2009/0311300 A1 | 12/2009 | Wittchow |
| 2009/0312807 A1 | 12/2009 | Boudreault et al. |
| 2009/0319035 A1 | 12/2009 | Terry |
| 2009/0324684 A1 | 12/2009 | Atanasoska et al. |
| 2009/0326638 A1 | 12/2009 | Atanasoska et al. |
| 2010/0008970 A1 | 1/2010 | O'Brien et al. |
| 2010/0010621 A1 | 1/2010 | Klocke |
| 2010/0010640 A1 | 1/2010 | Gerold et al. |
| 2010/0015206 A1 | 1/2010 | Flanagan et al. |
| 2010/0016940 A1 | 1/2010 | Shokoohi et al. |
| 2010/0021523 A1 | 1/2010 | Scheuermann et al. |
| 2010/0023112 A1 | 1/2010 | Borck et al. |
| 2010/0023116 A1 | 1/2010 | Borck et al. |
| 2010/0028436 A1 | 2/2010 | Ohrlander et al. |
| 2010/0030326 A1 | 2/2010 | Radhakrishman et al. |
| 2010/0034899 A1 | 2/2010 | Harder et al. |
| 2010/0042205 A1 | 2/2010 | Atanasoska et al. |
| 2010/0042206 A1 | 2/2010 | Yadav et al. |
| 2010/0047312 A1 | 2/2010 | Wittchow |

| | | | | | | |
|---|---|---|---|---|---|---|
| 2010/0047324 | A1 | 2/2010 | Fritz et al. | WO | 99/64580 | 12/1999 |
| 2010/0049146 | A1 | 2/2010 | Nielsen et al. | WO | 00/25841 | 5/2000 |
| 2010/0049296 | A1 | 2/2010 | Sarasam et al. | WO | 00/48660 | 8/2000 |
| 2010/0049299 | A1 | 2/2010 | Popowski et al. | WO | 00/51136 | 8/2000 |
| 2010/0049300 | A1 | 2/2010 | Harder | WO | 00/54704 | 9/2000 |
| 2010/0055151 | A1 | 3/2010 | Flanagan | WO | 00/66190 | 11/2000 |
| 2010/0057188 | A1 | 3/2010 | Weber | WO | 01/49338 | 7/2001 |
| 2010/0057197 | A1 | 3/2010 | Weber et al. | WO | 01/78906 | 10/2001 |
| 2010/0070024 | A1 | 3/2010 | Venturelli et al. | WO | 01/80920 | 11/2001 |
| 2010/0075162 | A1 | 3/2010 | Yang et al. | WO | 01/87371 | 11/2001 |
| 2010/0076544 | A1 | 3/2010 | Hoffmann et al. | WO | 02/45764 | 6/2002 |
| 2010/0076556 | A1 | 3/2010 | Tomantschger et al. | WO | 02/47739 | 6/2002 |
| 2010/0081735 | A1 | 4/2010 | Mao et al. | WO | 02/053202 | 7/2002 |
| 2010/0082092 | A1 | 4/2010 | Gerold | WO | 03/002243 | 1/2003 |
| 2010/0087910 | A1 | 4/2010 | Weber | WO | 03/013396 | 2/2003 |
| 2010/0087911 | A1 | 4/2010 | Mueller | WO | 03/035131 | 5/2003 |
| 2010/0087914 | A1 | 4/2010 | Bayer et al. | WO | 03/035134 | 5/2003 |
| 2010/0087915 | A1 | 4/2010 | Bayer et al. | WO | 03/035278 | 5/2003 |
| 2010/0087916 | A1 | 4/2010 | Bayer et al. | WO | 03/046062 | 6/2003 |
| 2010/0092535 | A1 | 4/2010 | Cook et al. | WO | 03/063733 | 8/2003 |
| 2010/0106243 | A1 | 4/2010 | Wittchow | WO | 03/094990 | 11/2003 |
| 2010/0119576 | A1 | 5/2010 | Harder et al. | WO | 2004/029313 | 4/2004 |
| 2010/0119581 | A1 | 5/2010 | Gratz et al. | WO | 2004/043292 | 5/2004 |
| 2010/0121432 | A1 | 5/2010 | Klocke et al. | WO | 2004/093643 | 11/2004 |
| 2010/0125325 | A1 | 5/2010 | Allen et al. | WO | 2005/025449 | 3/2005 |
| 2010/0125328 | A1 | 5/2010 | Flanagan | WO | 2005/065576 | 7/2005 |
| 2010/0131050 | A1 | 5/2010 | Zhao | WO | 2005/079335 | 9/2005 |
| 2010/0131052 | A1 | 5/2010 | Kappelt et al. | WO | 2005/110395 | 11/2005 |
| 2010/0161031 | A1 | 6/2010 | Papirov et al. | WO | 2005/118019 | 12/2005 |
| 2010/0217370 | A1 | 8/2010 | Scheuermann et al. | WO | 2006/008739 | 1/2006 |
| | | | | WO | 2006/060033 | 6/2006 |

FOREIGN PATENT DOCUMENTS

| | | | | | |
|---|---|---|---|---|---|
| AU | 2003 203 722 | 11/2003 | WO | 2006/060534 | 6/2006 |
| CA | 2 235 031 | 10/1998 | WO | 2006/065356 | 6/2006 |
| CA | 2 346 857 | 5/2000 | WO | 2006/077154 | 7/2006 |
| CA | 2 371 800 | 8/2000 | WO | 2006/080381 | 8/2006 |
| DE | 198 11 033 | 8/1999 | WO | 2006/097503 | 9/2006 |
| DE | 198 56 983 | 12/1999 | WO | 2006/104644 | 10/2006 |
| DE | 103 57 281 | 7/2005 | WO | 2006/108065 | 10/2006 |
| DE | 103 61 941 | 7/2005 | WO | 2007/005806 | 1/2007 |
| DE | 10 2006 38236 | 2/2008 | WO | 2007/013102 | 2/2007 |
| EP | 0 006 544 | 6/1979 | WO | 2007/018931 | 2/2007 |
| EP | 0 337 035 | 11/1993 | WO | 2007/024552 | 3/2007 |
| EP | 0 923 389 | 7/1998 | WO | 2007/035791 | 3/2007 |
| EP | 0 966 979 | 12/1999 | WO | 2007/079363 | 7/2007 |
| EP | 0 972 563 | 1/2000 | WO | 2007/079636 | 7/2007 |
| EP | 1 054 644 | 11/2000 | WO | 2007/082147 | 9/2007 |
| EP | 1 071 490 | 1/2001 | WO | 2007/139668 | 12/2007 |
| EP | 1 222 901 | 7/2002 | WO | 2008/003450 | 3/2008 |
| EP | 1 270 023 | 1/2003 | WO | 2008/034048 | 3/2008 |
| EP | 1 273 314 | 1/2003 | WO | 2008/034066 | 3/2008 |
| EP | 1 370 306 | 12/2003 | WO | 2008/036457 | 3/2008 |
| EP | 0 923 912 | 2/2004 | WO | 2008/036548 | 3/2008 |
| EP | 1 393 766 | 3/2004 | WO | 2008/036554 | 3/2008 |
| EP | 1 419 793 | 5/2004 | WO | 2008/062414 | 5/2008 |
| EP | 0 951 877 | 6/2004 | WO | 2008/092436 | 8/2008 |
| EP | 1 260 214 | 6/2004 | WO | 2008/106271 | 9/2008 |
| EP | 0 875 218 | 2/2005 | WO | 2008/117315 | 10/2008 |
| EP | 1632256 | 3/2006 | WO | 2008/118606 | 10/2008 |
| EP | 1 389 471 | 8/2006 | WO | 2009/045773 | 4/2009 |
| EP | 1 733 746 | 12/2006 | | | |
| EP | 1 752 167 | 2/2007 | | | |
| EP | 1 465 552 | 5/2007 | | | |
| EP | 1 835 042 | 9/2007 | | | |
| EP | 1 750 780 | 10/2007 | | | |
| EP | 1 562 565 | 3/2008 | | | |
| EP | 1 642 551 | 12/2008 | | | |
| EP | 1 653 885 | 4/2009 | | | |
| EP | 1 703 858 | 10/2009 | | | |
| EP | 2 139 535 | 1/2010 | | | |
| EP | 1 883 380 | 3/2010 | | | |
| EP | 2 189 169 | 5/2010 | | | |
| RU | 2 218 242 | 12/2003 | | | |
| WO | 93/04118 | 3/1993 | | | |
| WO | 97/11724 | 4/1997 | | | |
| WO | 98/29025 | 7/1998 | | | |
| WO | 98/48851 | 11/1998 | | | |
| WO | 99/33410 | 7/1999 | | | |
| WO | 99/47077 | 9/1999 | | | |

OTHER PUBLICATIONS

U.S. Appl. No. 60/826,002, filed Sep. 18, 2006, Girton et al.
U.S. Appl. No. 60/845,136, filed Sep. 15, 2006, Weber and Atanasoska.
U.S. Appl. No. 60/862,318, filed Oct. 20, 2006, Atanasoska et al.
"Best of the ACC Scientific Session 2002," *Rev. Cardiovasc. Med.*, 2002, 3(2):85-104.
"Chapter 2: Corrosion Theory and Corrosion Protection," *EM 1110-2-3400*, 1995, 8 pages.
"Galvanic cell" printout from wikipedia, 5 pages, printed on Aug. 16, 2010.
"*Gaivanicc corrosion*." http://www.corrosion-doctors.org/aircraft/galvdefi.htm, 3 pgs., printed Oct. 28, 2005.
"Galvanic series" printout from Wikipedia, p. 1 of 2, printed Oct. 28, 2005.
Aaltonen, "Atomic Layer Deposition of Noble Metal Thin Films," *University of Helsinki*, Apr. 8, 2005, pp. 1-71.

Aghion et al., "Newly Developed Magnesium Alloys for Powertrain Applications," *JOM*, 2003, p. 30.

Albion Research Notes, Newsletter, Oct. 1994, 3(4): 1-4.

Anand et al., "Ion-exchange resins: carrying drug delivery forward," *DDT*, 2001, 6: 905-914.

Anderson et al., "A new conductive polymer as a replacement for chrome conversion coatings," *2003 Aerospace Coatings Removel and Coatings Conference*,May 20-22, 2003, Colorado Springs, CO, 7 pages.

Andión et al., "Corrosion behaviour at the interface of steel bars embedded in cement slurries Effect of phenol polymer coatings," *Corrosion Science*, 2002, 44:2805-2816.

Antipov et al., "Polyelectrolyte Multilayer Capsule Permeability Control," *Colloids and Surfaces A: Physiochem. Eng. Aspects*, 2002, 198-200, 535-541.

Antipov et al., "Polyelectrolyte Multilayer Capsules as Vehicles with Tunable Permeability", *Advances in Colloid and Interface Science*, 2004, 111: 49-61.

Arts et al., "Polyphenols and disease risk in epidemiologic studies," *Am. J. Clin. Nutr.*, 2005, 81:317S-325S.

Artyukhin et al., "Layer-by-Layer Electrostatic Self-Assembly of Polyelectrolyte Nanoshells on Individual Carbon Nanotube Templates," *Langmuir*, 2004, 20:1442-1448.

Ashtari et al. "An efficient method for recovery of target ssDNA based on amino-modified silica-coated magnetic nanoparticles" *Talanta 67*. (2005). 548-554.

Atta, "Electrochemical synthesis, characterization and some properties of a polymer derived from thioflavin S.," *European Polymer Journal*, 2005, 41: 3018-3025.

Australian Government, Department of Health and Aging, "Horizon Scanning Technology Prioritising Summary—Biodegradable stents for coronary artery disease," *Australia and New Zealand Horizon Scanning Network (ANZHSN)*, Aug. 2007, pp. 1-13.

International Preliminary Report on Patentability in PCT/US07/78449 mailed Mar. 26, 2009, 9 pages.

International Preliminary Report on Patentability in PCT/US07/79841 mailed Apr. 30, 2009, 7 pages.

International Preliminary Report on Patentability in PCT/US08/86639 mailed Jun. 24, 2010, 2 pages.

International Search Report/Written in PCT/US07/79841 mailed Feb. 4, 2009, 11 pages.

International Search Report/Written Opinion in PCT/US07/60137 mailed Jul. 27, 2007, 20 pages.

International Search Report/Written Opinion in PCT/US07/78450 mailed Nov. 19, 2008, 17 pages.

International Search Report/Written Opinion in PCT/US07/88888 mailed Jul. 13, 2009, 24 pages.

International Preliminary Report on Patentability in PCT/US07/88888 mailed Jul. 30, 2009, 11 pages.

International Search Report/Written Opinion in PCT/US2008/86639 mailed Feb. 23, 2010, 8 pages.

International Preliminary Report on Patentability in PCT/US07/66568 mailed Oct. 23, 2008, 10 pages.

International Preliminary Report on Patentability in PCT/US07/75072 mailed Feb. 12, 2009, 9 pages.

International Search Report/Written Opinion in PCT/US07/78412 mailed Mar. 3, 2008, 10 pages.

International Search Report/Written Opinion in PCT/US09/49422 mailed Aug. 24, 2009, 10 pages.

International Search Report/Written Opinion in PCT/US08/75976 mailed Nov. 25, 2008, 20 pages.

International Search Report/Written Opinion in PCT/US2009/43326 mailed Aug. 6, 2009, 9 pages.

Bach et al., "Corrosion, Protection and Repassivation After the Deformation of Magnesium Alloys Coated With a Protective Magnesium Fluoride Layer," *JOM*, 2004, p. 343.

Bakkar et al., "Improving corrosion resistance of magnesium-based alloys by surface modification with hydrogen by electrochemical ion reduction (EIR) and by plasma immersion ion implantation (PIII)," *Corrosion Science*, 2005, 47:1211-1225.

Balasubramanian et al. "Dispersion and Stability Studies of Resorcinarene-Encapsulated Gold Nanoparticles." *Langmuir*, 2002, 1676-3681.

Bao, Y. et al. "Preparation of functionalized and gold-coated cobalt nanocrystals for biomedical applications." *Journal of Magnetism and Magnetic Materials*, 2005, 293:15-19.

Baurschmidt et al., "The Electrochemical Aspects of the Thrombogenicity of a Material," *J. Bioengineering*, 1977, 1:261-278.

Bekesi et al., "Efficient Submircon Processing of Metals with Femto," *Appl. Phys. A.*, Published Oct. 25, 2002, pp. 355-357.

Ben-Hamu et al., "Influence of Si, Ca and Ag addition on corrosion behaviour of new wrought Mg—Zn alloys," *Materials Science and Technology*, 2006, vol. 22, No. 10, pp. 1213-1218.

Bereket et al., "Electrochemical synthesis and anti-corrosive properties of polyaniline, poly(2-anisidine), and poly(aniline-co-2-anisidine) films on stainless steel," *Progress in Organic Coatings*, 2005, 54: 63-72.

Berkland et al., "Controlling Surface Nano-structure Using Flow-Limited Field-Injection Electrostatic Spraying (FFESS) of poly(D,L-lacide-*co*-glycolide)," *Biomaterials*, 2004, 25:5649-5658.

Bernkop-Schnurch, "Chitosan and its derivatives: potential excipients for peroral peptide delivery systems," *International J. of Pharmaceutics*, 2000, 194: 1-13.

Berry et al., "Functionalisation of magnetic nanoparticles for applications in biomedicine," *J. Phys. D: Appl. Phys.*, 2003, 36:R198-R206.

Biercuk et al., "Low-temperature atomic-layer-deposition lift-off method for microelectronic and nanoelectronic applications," *Applied Physics Letters*, vol. 83, No. 12, Sep. 22, 2003, pp. 2405-2407.

Blanusa et al., "Chelators as Antidotes of Metal Toxicity Therapeutic and Experimental Aspects," *Current Medicinal Chemistry*, 2005, vol. 12, pp. 2771-2794.

Bolz et al., "Effect of smooth, porous and fractal surface structure on the properties of an interface," *J. Materials Science: Materials in Medicine*, 1995, 844-848.

Bosiers et al., "Absorbable Metal stent for CLI in Infrapopliteal lesions: 1 year results," *CX 2005 Global Endovascular Forum*, Apr. 2005, pp. 1-23.

Brandau et al., "Nanoporous Ceramic Coatings for Synthesis of Radioactive Implants," *Journal of Nuclear Medicine Abstract Book*, Jun. 7, 2000, p. 244P, Abstract No. 1076.

Brückner et al., "Metal plasma immersion ion implantation and deposition (MPIIID): chromium on magnesium," *Surface and Coatings Technology*, 1998, 103-104, pp. 227-230.

Brunatto and Muzart, "Influence of the gas mixture flow on the processing parameters of hollow cathode discharge ion sintering," *J. Phys. D.: Appl. Phys.*, 2007, 40: 3937-3944.

Brunner et al., "Porosity Tailored Growth of Black Anodic Layers on Magnesium in an Organic Electrolyte," *Journal of the Electrochemical Society*, vol. 156 (2), Dec. 12, 2008, pp. C62-C66.

Buescher et al., "Characterization of Wet-Chemically Nanostructured Stainless Steel Surfaces," *Mat. Res. Soc. Symp. Proc.*, 2001, 676:1-6.

Caruso et al., "Ultrathin Molybdenum Polyoxometalate-Polyelectrolyte Multilayer Films," *Langmuir*, 1998, 14:3462-3465.

Casan-Pastor et al., "Polyoxometalates: From Inorganic Chemistry to Materials Science," *Frontiers in Bioscience*, 2004, 9:1759-1770.

Chaieb et al., "Inhibition of the corrosion of steel in 1 M HCl by eugenol derivatives," *Applied Surface Science*, 2005, 246:199-206.

Chang et al., "Effect of Heat Treatment on Corrosion and Electrochemical behavior of Mg—3Nd—0.2Zn—0.4Zr (wt. %) alloy," *Science Direct, Electrochimica Acta 52*, 2007, 3160-3167.

Chang et al., "Templated sytheis of Gold-iron Alloy nanoparticles using pulsed laser deposition," *Nanotechnology*, vol. 17, 2006, pp. 5131-5135.

Changwen et al., "Polyoxometalate-based organic-inorganic hybrid materials," 2004, *Sol-Gel*, p. 1.

Chen et al., "Laser Cladding of Mg20A18o Powder on ZM5 Magnesium Alloy," *Corrosion Engineering, Science and Technology*, 2007, vol. 42, No. 2, pp. 130-136.

Cheng et al., "Electrogeneration and electrochemical properties of hybrid materials: polypyrrole doped with polyoxometalates $PW_{12-x}Mo_xO_{40}{}^{3-}$(x=0,3,6,12)," *Synthetic Metals*, 2002, 129: 53-59.

Cho et al., "Gold-coated iron nanoparticles: a novel magnetic resonance agent for $T_1$ and $T_2$ weighted imaging," *Nanotechnology*, vol. 17, 2006, pp. 640-644.

Chou et al., "Electrochemical treatment of mouse and rat fibrosarcomas with direct current," *Bioelectromagnetics*, 1997, 18:14-24.

Clemente-Leon et al., "Hybrid Langmuir-Blodgett Films Formed by Alternating Layers of Magnetic Polyoxometalate Clusters and Organic Donor Molecules—Towards the Preparation of Multifunctional Molecular Materials," *Adv. Mater.*, 2001, 13:574-577.

Cogger et al. "An Introduction to Electrochemical Impedance Measurement," *Solartron Analytical*, 1999, 2-14.

Conolly et al., "X-Ray microtomography studies of localized corrosion and transitions to stress corrosion cracking," *Materials Science and Technology*, 2006, vol. 22, No. 9, pp. 1076-1085.

Costa et al., "The effect of the magnetic field on the corrosion behavior of Nd—Fe—B permanent magnets." *Journal of Magnetism and Magnetic Materials*, 278, 2004, pp. 348-358.

Damen et al., "Paclitaxel esters of malic acid as prodrugs with improved water solubility," *Bioorganic & Medicinal Chemistry*, 2000, 8: 427-432.

Damiani et al., "Vasorelaxant effects on eugenol on rat thoracic aorta," *Vascular Pharmacol.*, 2003, 40:59-66.

Davies, "Changing the salt, changing the drug," *The Pharmaceutical Journal*, 2001, 266: 322-323.

De Geest et al., "Self-rupturing Microcapsules," *Adv. Mater.*, 2005, vol. 17, pp. 2357-2361.

de Witte, "Analysis of the principal component of external casing corrosion in deep wells," *J. Appl. Electrochem.*, 1985, 15: 325-334.

Dexter, "Galvanic Corrosion," MAS Note, University of Delaware Sea Grant Marine Advisory Service, 2003.

Di Mario et al., "Drug-eluting bioabsorbable magnesium stent," *J. Interventional Cardiol.*, 2004, 17(6): 391-395.

Di Mario et al., "MOONLIGHT: a controlled registry of an iridium oxide-coated stent with angiographic follow-up," *Int. J. Cardiol.*, 2004, 95:329-331.

Dowling et al., "Anti-bacterial silver coatings exhibiting enhanced activity through the addition of Platinum," *Surf. & Coatings Tech.*, 2003, 163-164:637-640.

Duncan et al., "Polymer-drug conjugates, PDEPY and PELT: basic principles for design and transfer from the laboratory to clinic," *Journal of Controlled Release*, 2001, 74: 135-146.

Duncan, "The dawning era of polymer therapeutics," *Nature Reviews/Drug Discovery*, 2003, 2: 347-360.

Duygu, "Controlled Release Systems," http://www.biomed.metu.edu.tr/courses/term_papers/contr-rel-sys_duygu.htm (Dec. 30, 2005).

Eggebrecht et al., "Novel Magnetic Resonance-Compatible Coronary Stent: The Absorbable Magnesium-Alloy Stent," *Circulation*, 2005, 112: 303-304.

Erbel et al., "Absorbierbare Stents-Eine Vielversprechende Neuerung?" *Urban & Vogel*, No. 4, 2007, pp. 308-319.

Erbel et al., "Temporary scaffolding of coronary arteries with bioabsorbable magnesium stents: a prospective, non-randomised multicentre trial," *Lancet*, 2007, vol. 369, pp. 1869-1875.

Erne et al., "The Road to Bioabsorbable Stents: Reaching Clinical Reality?" *Cardio Vascular and Interventional Radiology*, Sep. 26, 2005, pp. 11-16.

International Preliminary report on Patentability in PCT/US2007/078417, mailed Mar. 26, 2009, 8 pages.

International Preliminary Report on Patentability, in PCT/US2007/078407, mailed Mar. 26, 2009, 6 pages.

European Search Report from EP 10159664.1, mailed Jun. 4, 2010, 3 pages.

International Preliminary Report on Patentability in PCT/US05/16600 mailed Nov. 30, 2006, 7 pages.

International Search Report/Written Opinion in PCT/US05/16600 mailed May 4, 2006, 15 pages.

International Preliminary Report on Patentability in PCT/US07/78476 mailed Mar. 26, 2009, 7 pages.

International Preliminary Report on Patentability in PCT/US07/78411 mailed Feb. 4, 2009, 8 pages.

International Preliminary Report on Patentability in PCT/US07/78412 mailed Apr. 2, 2009, 7 pages.

International Preliminary Report on Patentability in PCT/US07/78505 mailed Mar. 26, 2009, 7 pages.

International Preliminary Report on Patentability in PCT/US07/78450 mailed Mar. 26, 2009, 7 pages.

Falotico, "Cordis Fully Bioabsorbable Stent Program," *Euro PCR09*, May 22, 2009, pp. 1-21.

Fan et al., "Influence of Lanthanum on the microstructure, mechanical property and corrosion resistance of magnesium alloy," *J. Mater Sci*, 2006, vol. 41, pp. 5409-5416.

Fan et al., "Metallic Stents Coated with Bioabsorable Polymers," *Cardiac Interventions Today*, Jun./Jul. 2009, pp. 42-49.

Farhat et al., "Corrosion Control Using Polyelectrolyte Multilayers," *Electrochemical and Solid State Letters*, 2002, 5(4):B13-B15.

Feng et al., "Sonochemical preparation of photochromic nanocomposite thin film based on polyoxometalates well dispersed in polyacrylamide," *Journal of Solid State Chemistry*, 2002, 169: 1-5.

Feng et al., "Superplasticity and texture of SiC whiskers in a magnesium-based composite," *Scripta Materialia*, 2005, 53: 361-365.

Ferguson et al., "Corrosion—Fatigue Performance of Magnesium Alloys," *International Journal of Modern Physics B*, vol. 17, Nos. 8 & 9, 2003, pp. 1601-1607.

Fernando, "Review of Corrosion and Corrosion Control of Magnesium Alloys and Composites," *J. Mater. Eng.*, 1989, 11:299-313.

Fischer et al., "Hydrogen in magnesium alloys and magnesium interfaces: preparation, electronic properties and interdiffusion," *J. Less—Common Metals*, 1991, 172:808-815.

Fontenier et al., "Study of a 'Platinum-Magnesium' Cell to Supply Current to a Pacemaker," *Bioelectrochemistry and Bioenergetics*, 1975, 2(2):106-123.

Fraunhofer EZRT, "Quantitative material analysis by dual energy computed tomography for industrial NDT applications," 2009, 1 pg.

Fraunhofer IIS—Poster (German), "Prinzip der hochauflösenden Comptuertomographie," 2009, 1 page.

Frei, "On the Role of Vitamin C and Other Antioxidants in Atherogenesis and Vascular Dysfunction," *Proceedings—Society for Experimental Biology and Medicine*, 1999, 222:196-204.

Gabrielli, Claude. "Use and Applications of Electrochemical Impedance Techniques," *Solartron Analytical*, 1997, 1-102.

Garner et al., "Polypyrrole-heparin composites as stimulus-responsive substrates for endothelial cell growth," *J. Biomed. Mater. Res.*, 1999, 44: 121-129.

Gettleman et al., "Measurement of in vivo corrosion rates in baboons, and correlation with in vitro tests," Journal of Dental Research, 1980, 59: 689-707.

Gettleman et al., "Materials Science: Measurement of in vivo Corrosion Rates in Baboons, and Correlation with in vitro Tests," *Journal of Dental Research*, 1980, vol. 59, pp. 689-707.

Gomes et al., "Alternative tissue engineering scaffolds based on starch: processing methodologies, morphology, degradation and mechanical properties," *Materials Science and Engineering C*, 2002, 20:19-26.

Grassi et al., "Short-term administration of dark chocolate is followed by a significant increase in insulin sensitivity and a decrease in blood pressure in healthy persons," *Am. J. Clin. Nutr.*, 2005, 81(3):611-614.

Gray and Luan, "Protective coatings on magnesium and its alloys—a critical review," *J. Alloys Compounds*, 2002, 336:88-113.

Griffiths et al., "Future devices: bioabsorbable stents," *Br. J. Cardiol. (Acute & Interventional Cardiology)*, 2004, 11: AIC80-AIC84.

Grube, "Bioabsorbable Stents—The Boston Scientific & REVA Technology," *EuroPCR 2009*, 2009, pp. 1-27.

Gu et al., "In vitro Corrosion and biocompatibility of binary magnesium alloys," *Biomaterials*, vol. 30, 2009, pp. 484-498.

Guo et al., "Manipulation of single-wall carbon nanotubes into aligned molecular layers," *Chem. Phys. Lett.*, 2002, 362:314-318.

Guo et al., "Multi-layer LB films of single-wall carbon nanotubes," *Physica B*, 2002, 323:235-236.

Gupta et al., "Nanometer spaced electrodes using selective area atomic layer deposition," *Applied Physics Letters*, vol. 90, 2007, pp. 1-4.

Gurib-Fakim, "Medicinal plants: Traditions of yesterday and drugs of tomorrow," *Molecular Aspects of Medicine*, 2006, 27:1-93.
Haenzi et al., "Design strategy for microalloyed ultra-ductile Mg alloys," 2009, *Phil. Mag. Letters*, 89(6): 377-390.
Haenzi et al., "Design strategy for new biodegradable Mg—Y—Zn alloys for medical applications," *Int. J. Mat. Res.*, 2009, 100: 1127-1136.
Haenzi et al., "On the biodegradation performance of an Mg—Y—RE alloy with various surface conditions in simulated body fluid," *Acto Biomat.*, 2009, 5: 162-171.
Haferkamp et al., "Magnesium-Base-Alloys as Implant-Material Steps to the Production of Thin Components," *Magnesium*, 2000, 159-164.
Hamu et al., "Influence of Si, Ca and Ag addition on corrosion behavior of new wrought Mg—Zn alloys," 2006, 22(10): 1213-1218.
Hänzi et al., "Design strategy for microalloyed ultra-ductile magnesium alloys," *Philosophical Magazine letters*, vol. 89, No. 6, Jun. 2009, pp. 377-390.
Hänzi et al., "Design strategy for new biodegradable Mg—Y—Zn alloys for medical applications," *Int. J. Mat. Res.*, vol. 100, 2009, pp. 1127-1136.
Hänzi et al., "On the biodegradation performance of an Mg—Y—Re alloy with various surface conditions in simulated body fluid," *Acta Biomaterialia*, vol. 5, 2009, pp. 162-171.
Hague et al. "Bioabsorption Qualities of Chitosan-absorbable Vascular Templates," *Current Surgery*, 2001, 58(1): 77-80.
Hau et al., "Surface-Chemistry Technology for Microfluidics," *J. Micromech. Microeng.*, 2003.13:272-278.
Heismann et al., "Density and atomic number measurements with spectral x-ray attenuation method," *Journal of Applied Physics*, vol. 94, No. 3, Aug. 1, 2003, pp. 2073-2079.
Hermawan et al., "Developments in metallic biodegradable stents," *Acta Biomaterialia*, 2010, 6: 1693-1697.
Hermawan et al., "Degradable metallic biomaterials: Design and development of Fe—Mn alloys for stents," *Wiley InterScience: Article*, Apr. 19, 2008, pp. 1-12.
Hermawan et al., "Degradation Behaviour of Metallic Biomaterials for Degradable Stents," *Advanced Materials Research*, 2007, 15-17:113-118.
Hermawan et al., "Development of Degradable Fe—35Mn Alloy for Biomedical Application," *Advanced Material Research*, 2007, 15-17:107-112.
Hermawan et al., "Fe—Mn Alloys for Metallic Biodegradable Stents: Degradation and Cell Viability Studies," *Acta Biomaterialia*, Manuscript, Mar. 27, 2009, pp. 1-30.
Hermawan, et al., "Iron-Manganese: new class of metallic degradable biomaterials prepared by powder metallurgy," *Powder Metallurgy*, 2008, 51(1):38-45.
Heublein et al., "Biocorrosion of magnesium alloys: a new principle in cardiovascular implant technology?" *Heart*, 2003, 89:651-656.
Heublein et al., "Degradation of Metallic Alloys—A New Principle in Stent Technology?" *The American Journal of Cardiology, Eleventh Annual Symposium Transcatheter Cardiovascular Therapeutics Abstracts*, Sep. 22, 1999.
Heublein et al., "Bio-corrosion—a new principle for temporary cardiovascular implants?" *European Heart Journal, Journal of the European Society of Cardiology*, 2000, vol. 21, p. 286, Abstract No. P1605.
Heublein et al., "Local Tissue Engineering by Biocorrosion Vision or Reality?" *The American Journal of Cardiology, TCT Abstracts/Poster*, Oct. 16, 2000.
Hildebrandt et al., "Prevention of surface encrustation of urological implants by coating with inhibitors," *Biomaterials*, 2001, 22:503-507.
Holclajtner-Antunovic et al., "Study of some polyoxometallates of Keggin's type as potention antitumour agents," *Jugoslov Med. Biohem.*, 2004, 23: 25-30.
Hourng et al., Influence of multisteps thermal control in metal powder injection moulding process, *Powder Metallurgy*, 2008, 51: 84-89.
Huang et al., "A Review on Polymer Nanofibers by Electro-spinning and their Applications in Nanocomposites," 2003, 63:2223-2253.

Hutten, A. et al. "Ferromagnetic FeCo nanoparticles for biotechnology". (2005) *Journal of Magnetism and Magnetic Materials* 293:93-101).
Iakovou et al., "Incidence, Predictors, and Outcome of Thrombosis Successful Implantation of Drug-Eluting Stents," *JAMA*, 2005, 293(17): 2126-2130.
Ignat et al., "Magnesium alloys (WE43 and ZE41) characterization for laser applications," *Applied Surface Science*, 2004, 233:382-391.
Iida et al. "Surface modification of of λFe2O3 nanoparticles with aminopropylsilyl groups and interparticle linkage with with a,w-Dicarboxylic Acids". *Electrochimica Acta*, 2005, 855-859.
Imgrund, "Evaluation of metal injection moulding (MIM) and extrusion as processing technology for biodegradable stents. A 208143: Final report for phase I MIM of Fe and Fe—Si powders and sample characterisation," Aug. 15, 2008, *Fraunhofer Institut Fertigungstechnik Material forschung*, 18 pages.
Integran, "Biodegradable Nanometallic Intracoronary Stents," May 12, 2009, 1 page.
Integran, "Biodegradable Nanometallic Intracoronary Stents," Proposal, May 12, 2009, 1 page.
International Preliminary Report on Patentability in PCT/US07/60137 mailed Jul. 17, 2008, 7 pages.
International Preliminary Report on Patentability in PCT/US07/73839 mailed Apr. 2, 2009.
International Preliminary Report on Patentability in PCT/US07/78429 mailed Apr. 2, 2009.
International Preliminary Report on Patentability in PCT/US07/78475 mailed Mar. 26, 2009, 8 pages.
International Preliminary Report on Patentability in PCT/US2007/078479, mailed Mar. 26, 2009, 8 pages.
International Search Report / Written Opinion in PCT/US09/046750 mailed Jul. 20, 2010, 14 pages.
International Search Report and Written Opinion in PCT/US07/78449, mailed Jan. 13, 2009, 15 pages.
International Search Report and Written Opinion in PCT/US07/78475, mailed Feb. 4, 2009, 14 pages.
International Search Report and Written Opinion in PCT/US07/78476, mailed Jan. 28, 2009, 29 pages.
International Search Report and Written Opinion mailed Jan. 25, 2008 in PCT/US07/75072, 14 pages.
International Search Report and Written Opinion in PCT/US2007/078417, mailed Jan. 22, 2009, 18 pages.
International Search Report and Written Opinion in PCT/US2007/078479, mailed Dec. 30, 2008, 12 pages.
International Search Report for PCT/US05/16600 mailed May 4, 2006, 4 pages.
International Search Report for PCT/US07/66568 dated Oct. 8, 2007, 15 pages.
International Search Report from PCT/US 03/20215, mailed Nov. 11, 2003, 4 pages.
International Search Report/Written Opinion in PCT/US07/73839 mailed Apr. 16, 2008, 16 pages.
International Search Report/Written Opinion in PCT/US07/78411 mailed Mar. 6, 2008, 12 pages.
International Search Report/Written Opinion in PCT/US07/78429 mailed Mar. 28, 2008, 14 pages.
International Search Report/Written Opinion in PCT/US07/78505 mailed Mar. 4, 2008, 10 pages.
International Search Report/Written Opinion in PCT/US2007/078407, mailed Mar. 26, 2008, 10 pages.
Ito et al., "Antioxidant action of eugenol compounds; role of metal ion in the inhibition of lipid peroxidation," *Food Chem. Toxicol.*, 2005, 43:461-466.
Ivanova and Ivanov, "Mechanisms of the extracellular antioxidant defend," *Experimental Pathology and Parasitology*, 2000, 4:49-59.
Jabara et al., "Bioabsorbable Stents: The Future is Near," *Cardiac Interventions Today*, Jun./Jul. 2009, pp. 50-53.
Jabara, "Poly-anhydride based on salicylic acid and adipic acid anhydride," Glimpse into the future: bioabsorbable stents-aimint to restore vascular integrity, *Euro PCR09*, 2009, pp. 1-34.
James A. Plambeck, "Electrolytic Processes of Nonmetals," *Chemical Sciences*, 1995, 2 pages.

Jiang et al., "Corrosion protection of polypyrrole electrodeposited on AZ91 magnesium alloys in alkaline solutions," *Synthetic Materials*, 2003, 139: 335-339.

Jiang et al., "Effect of $TiB_2$ particulate on partial remelting behavior of Mg—11Al—0.5Zn matrix composite," *Materials Science and Engineering A*, 2004, 381: 223-229.

Jiang, "A review of wet impregnation—An alternative method for the fabrication of high performance and nano-structured electrodes of solid oxide fuel cells," *Materials Science and Engineering A*, 2006, 418:199-210.

Kaesel et al., "Approach to Control the Corrosion of Magnesium by Alloying," *Magnesium: Proceedings of the 6th International Conference Magnesium Alloys and Their Applications*, 2004, pp. 534-539.

Kainer, "Magnesium alloys and technology," Wiley VCH, 2003, 119 pages.

Kaya et al., "Microstructure and Corrosion Resistance of Alloys of the Mg—Zn—Ag System," *Metal Science and Heat Treatment*, 2006, 48(11-12): 524-530.

Kean and Davies, "Cathodic Protection," 7 pages, 1981; http://www.npl.co.uk/upload/pdf/cathodic_protection.

Kececioglu, "Zur Biokompatibilitat eines neu entwickelten Stentmaterials aus korrodierbarem Reineisen," Jan. 25, 2007, pp. 1-131, *Ruhr-Universitat-Bochum*.

Kidambi et al., "Selective depositions on polyelectrolyte multilayers: self-assembled monolayers of m-dPEG acid as molecular template," *J. Am. Chem. Soc.*, 2004, 126: 4697-4703.

Kim et al., "Comprehensive study on vitamin C equivalent antioxidant capacity (VCEAC) of various polyphenols in scavenging a free radical and its structural relationship," *Crit. Rev. Food Sci. Nutr.*, 2004, 44(4):253-273.

Kim et al., "Effect of Anti-Oxidant (Carvedilol and Probucol) Loaded Stents in a Porcine Coronary Restenosis Model," *Circ. J.*, 2005, 69:101-106.

Kokubo et al., "How useful is SBF in predicting in vivo bone bioactivity?" *Biomaterials*, 2006, 27: 2907-2915.

Kong et al., "Polyelectrolyte-functionalized multiwalled carbon nanotubes: preparation, characterization and layer-by-layer self assembly," *Polymer*, 2005, 46:2472-2485.

Kumar et al., "Polyanhydrides: an overview," *Advanced Drug Delivery Reviews*, 2002, 54:889-910.

Kurth et al., "Multilayer on Solid Planar Substrates: From Structure to Function", *Multi-layer Thin Films Sequential Assembly of Nanocomposite Materials*, 2003, Chapter 14, pp. 393-426.

Kurth et al., "Ultrathin Composite Films Incorporating the Nanoporous Isopolyoxomolybdate 'Keplerate' $(NH_4)_42[Mo_{132}O_{372}(CH_3COO)_{30}(H_2O)_{72}]$," *Chem. Mater.*, 2000, 12:2829-2831.

Kutsenko et al., "Structural Changes in Mg Alloy induced by plasma immersion ion implantation of Ag," *Acta Materialia*, 2004, 52:4329-4335.

LaFont, "Arterial Remodeling Technologies: Bioresorbable Stents," *Euro PCR09*, 2009, pp. 1-28.

Lambert et al., "Inhibition of carcinogenesis by polyphenols: evidence from laboratory investigations," *Am. J. Clin. Nutr.*, 2005, 81(suppl):284S-291S.

Lee et al., "Retentive and compressive strengths of modified zinc oxide-eugenol cements," *J. Dentistry*, 2000, 28:69-75.

Lee, J. et al. "Simple synthesis of mesoporous carbon with magnetic nano particles embedded in carbon rods". (2005) Carbon 43:2536-2543.

Lee, Sang-Yup et al. "Surface modification of magnetic nanoparticles capped by oleic acids: Characterization and colloidal stability in polar solvents" *Journal of Colloid and Interface Science* 293 (2006) 401-408.

Levesque et al., "Design of pseudo-physiological test bench specific to the development of biodegradable metallic biomaterials," *Acta Biomaterialia*, 2008, 4:284-295.

Li et al., "Effects of Direct Current on Dog Liver: Possible Mechanisms for Tumor Electrochemical Treatment," *Bioelectromagnetics*, 1997, 18:2-7.

Li et al., "Photoacoustic Tomography and Sensing in Biomedicine," *Phys. Med. Biol.*, 2009, 54:59-97.

Li, "Poly(L-glutamic acid)-anticancer drug conjugates," *Advanced Drug Delivery Reviews*, 2002, 54: 695-713.

Liao et al., "Fabrication of porous biodegradable polymer scaffolds using a solvent merging/particulate leaching method," *J. Biomed. Mater. Res.*, 2002, 59:676-681.

Lin et al., "Micropatterning proteins and cells on polylactic acid and poly(lactide-*co*-glycolide)," *Biomaterials*, 2005, 26:3655-3662.

Liu et al., "Characterizations of polypyrrole (PPy) nano-tubules made by templated ac electropolymerization," *European Polymer Journal*, 2005, 41: 2117-2121.

Liu et al., "Layer-By-Layer Ionic Self-Assembly of Au Colloids Into Multilayer Thin-Films with Bulk Metal Conductivity," *Chemical Physics Letters*, 1998, 298:315-319.

Liu et al., "Functional Polyoxometalate Thin Films via Electrostatic Layer-by-Layer Self-Assembly," *Journal of Cluster Science*, 2003, 14:405-419.

Liu et al., "Sol-gel deposited TiO2 film on NiTi surgical alloy for biocompatibility improvement," *Thin Solid Films*, 2003, 429:225-230.

Liu, *Introduction to Corrosion and Protection*, Corrosion and Protection Centre, School of Materials, The University of Manchester, 2006, 36 pages.

Lu et al. "Magnetic Switch of Permeability for Polyelectrolyte Microcapsules Embedded with Co@Au Nanoparticles". *American Chemical Society*. 2004.

Lu et al., "Theoretical analysis of calcium phosphate precipitation in simulated body fluid," *Biomaterials*, 2005, 26:1097-1108.

Macias et al., "Electrospun mesoporous metal oxide fibers," *Microporous and Mesoporous Materials*, 2005, 86: 1-13.

Maeng et al., "Negative Vascular Remodelling after Implantation of Bioabsorbable Magnesium Alloy Stents in Porcine Coronary Arteries: A randomized Comparison with Bare-Metal and Sirolimus-Eluting Stents," *Heart*, 2009, 95:241-246.

Maier et al., "High concentrations of magnesium modulate vascular endothelial cell behaviour in vitro," *Biochim. Biophys. Acta*, 2004, 1689:6-12.

Mamedov et al., "Molecular Design of Strong Single-Wall Carbon Nanotube/Polyelectrolyte Multilayer Composites," *Nature Materials*, 2002, 1:190-194.

Maendl, "Zerstaubungsabscheidung von Mg-Legierungen," *Leibniz-Institut fur Oberflachenmodifizierung*, 2001, pp. 1-17.

Mani et al., "Coronary Stents: A materials perspective," *Biomaterials*, 2007, 28:1689-1710.

Mansfeld, Florian. "Analysis and Interpretation of EIS Data for Metals and Alloys," *Solartron Analytical*, 1999, 1-77.

Marijan et al. "Surface Modification of Stainless Steel-304 Electrode. 2. An Experimental Comparative Study of Electrochemically, Hydrothermally and Chemically Modified Oxide Films." *CCACAA*, 1999, 72(4) 751-761.

Markman, "Absorbable Coronary stents," *The Lancet*, Jun. 2, 2007, 369:1839-1840.

Massaro et al., "Comparative Investigation of the surface properties of commerical titanium dental implants. Part 1: chemical composition," *Journal of Materials Science: Materials in Medicine*, vol. 13, 2002, pp. 535-548.

Matsuoka et al., "Hyperthermia Using Magnetite Cationic Liposomes for Hamster Osteosarcoma," *Biomagnetic Research and Technology*, Mar. 25, 2004, pp. 1-6.

Medical Device Daily, "Conor Cites Positive 12-month Results for Its CoStar Stent", May 2005 (1 page).

Meng Han, "Laser nitriding of metals: Influences of the ambient pressure and the pulse duration," 2001, Dissertation, Georg-August-Universität Göttingen, 134 pages.

Miao et al., "Porous Calcium Phosphate Ceramics prepared by coating polyurethane foams with Calcium phosphate cements," *Materials Letters*, vol. 58, 2004, pp. 397-402.

Middleton and Tipton, "Synthetic Biodegradable Polymers as Medical Devices," http://www.devicelink.com/mpb/archive/98/03/002.html, Mar. 1998, 9 pages.

Mihailovic et al., "Unusual Magnetic State in Lithium-Doped $MoS_2$ Nanotubes," *Phys. Rev. Lett.*, 2003, 90 146401-1-4.

Mikos and Temenoff, "Formation of highly porous biodegradable scaffolds for tissue engineering," *Electronic Journal of Biotechnology*, 2000, 3(2):114-119.

Mohanty et al. "Evaluation of soft tissue response to a poly[urethane urea]," *Biomaterisl*, 1992, 13(10):651-656.

Mohanty et al., "Effect of *Curcuma longa* and *Ocimum sanctum* on myocardial apoptosis in experimentally induced myocardial ischemic-reperfusion injury," *BMC Complementary and Alternative Medicine*, 2006, 6:3-14.

Molnar and Garai, "Plant-derived anti-inflammatory compounds affect MIF tautomerase activity," *International Immunopharmacology*, 2005, 5:849-856.

Moskaug et al., "Polyphenols and glutathione synthesis regulation," *Am. J. Clin. Nutr.*, 2005, 81(suppl):277S-283S.

Mueller et al., "Control of smooth muscle cell proliferation by ferrous iron," *Biomaterials*, vol. 27, 2006, pp. 2193-2200.

Mueller et al., "Magnesium and its Alloys as Degradable Biomaterials, Corrosion Studies Using Potentiodynamic and EIS Electrochemical Tenchiques," *Materials Research*, 2007, 10(1): 5-10.

Mueller et al., "Preparation of SBF with different $HCO_3$ content and its influence on the composition of biomimetic apatites," *Acta Biomaterialia*, 2006, 2:181-189.

Munoz et al., "Interactive Effects of Albumin and Phosphate Ions on the Corrosion of CoCrMo Implant Alloy," *Journal of the Electrochemical Society*, 2007, 154(10):562-570.

Naderi et al., "Effect of some volatile oils on the affinity of intact and oxidized low-density lipoproteins for adrenal cell surface receptors," *Mol. Cell. Biochem.*, 2004, 267:59-66.

Nair and Laurencin, "Biodegradable polymers as biomaterials," *Prog. Polym. Sci.*, 2007, 32: 762-798.

Nguyen et al., "Mechanism for protection of iron corrosion by an intrinsically electronic conducting polymer," *Journal of Electroanalytical Chemistry*, 2004, 572: 225-234.

Ni et al., "Cellular localization of antiviral polyoxometalates in J774 macrophages," *Antiviral Research*, 1995, 32: 141-148.

Niemeyer et al., "Magnesium alloys as biodegradable metallic implant materials for cardiovascularic and orthopaedic surgery," *Euromat 2001, 7th European Conference on Advanced Materials and Processes*, Jun. 10-14, 2001.

Niinisto, "Atomic Layer deposition: A key technology for the controlled growth of oxide thin films for advanced applications," *Proc. Estonian Acad. Sci. Phys. Math.*, 2003, 52(3):266-276.

Nilsson et al., "Development of a dosage method for electrochemical treatment of tumours: a simplified mathematical model," *Bioelectrochemistry and Bioenergetics*, 1998, 47:11-18.

Ogata et al., "A novel anti-tumor agent, polyoxomolybdate induces apoptotic cell death in AsPC-1 human pancreatic cancer cells," *Biomedicine & Pharmacotherapy*, 2005, 59: 240-244.

Onuma et al., "Everolimus-eluting bioabsorbable stent," *Euro PCR09*, May 22, 2009, pp. 1-28.

Ormiston et al., "Bioabsbabable Coronary Stents," *Circulation Cardiovasc Intervent*, vol. 2, 2009, pp. 255-260.

Ou et al., "Protective effects of eugenol against oxidized LDL-induced cytotoxicity and adhesion molecule expression in endothelial cells," *Food Chem. Toxicol.*, 2006, 44:1485-1495.

Ouerd et al., "Reactivity of Titanium in Physiogoical Medium—I. Electrochemical Characterization of the Metal/Protein Interface," *Journal of the Electrochemical Society*, vol. 154, No. 10, 2007, pp. 593-601.

Oyane et al., "Preparation and assessment of revised simulated body fluids," *Wiley Periodicals, Inc.*, 2003, pp. 188-195.

Paliwoda-Porebska et al., "On the development of polypyrrole coatings with self-healing properties for iron corrosion protection," *Corrosion Science*, 2005, 47: 3216-3233.

Park et al., "Microstructural change and precipitation hardening in melt-spun Mg—X—Ca alloys," *Science and Technology of Advanced Materials*, 2001, 2:73-78.

Peeters et al., "Preliminary Results after Application of Absorbable Metal Stents in Patients with Critical Limb Ischemia," *J. Endovasc Ther*, 2005, 12:1-5.

Peeters, et al., "Preliminary Data on Absorbable Metal Stents," *MEET 2006*, Jun. 2006, pp. 1-30.

Peuster et al. "Long-term biocompatibility of a corrodible peripheral iron stent in the porcine of descending aorta," *Biomaterials*, 2006, 4955-4962.

Peuster et al., "A novel approach to temporary stenting: degradable cardiovascular stents produced from corrodible metal-results 6-18 months after implantation into New Zealand white rabbits," *Heart*, 2001, 86(5):563-569.

Peuster et al., "Are resorbable implants about to become a reality," *Cardiol Young*, 2006, 16:107-116.

Pinto Slattow et al., "Optical coherence tomography and intravascular ultrasound imaging of bioabsorbable magnesium stent degradation in porcine coronary arteries," *Cardiovascular Revascularization Medicine 9*, (2008) pp. 248-254.

Prasse et al., "Electric Anisotropy of Carbon Nanofibre/Epoxy Resin Composites Due to Electric Field Induced Alignment," *Composites Science and Technology*, 2003, 63:1835-1841.

Purushothaman et al. "Reducing Mass-Transport Limitations by Application of Special Pulsed Current Modes". *Journal of the Electrochemical Society*. 152 (4), 2005, J33-J39.

Qasem et al., "Kinetics of paclitaxel 2'-N-methylpyridinium mesylate decomposition," *AAPS PharmSciTech*, 2003, 4(2), Article 21, 8 pages.

Quinard et al., "Development of metal/polymer mixtures for micro powder injection moulding," *10th ESAFORM Conference on Material Forming*, 2007, pp. 933-939.

Qureshi et al., "The emerging role of iron, zinc, copper, magnesium and selenium and oxidative stress in health and diseases," *Biogenic Amines*, vol. 19, No. 2, 2005, pp. 147-169.

Raman et al., "Laser assisted modification of surface microstructure for localised corrosion resistance of magnesium alloys," *Surface Engineering*, 2007, 23(2): 107-111.

Ratnam et al., "Role of antioxidants in prophylaxis and therapy: A pharmaceutical perspective," *J. Controlled Release*, 2006, 113:189-207.

Reece et al., "Metal transport studies on inherently conducting polymer membrances containing cyclodextrin dopants," *Journal of Membrane Science*, 2005, 249: 9-20.

Remskar et al., "Self-Assembly of Subnanometer-Diameter Single-Wall $MoS_2$ Nanotubes," *Science*, 2001, 292:479-481.

Ren et al., "Variations of dose and electrode spacing for rat breast cancer electrochemical treatment," *Bioelectromagnetics*, 2001, 22(3):205-211.

Rettig et al., "Composition of corrosion layers on a magnesium rare-earth alloy in simulated body fluids," *Journal of Biomedical Materials Research Part A*, Oct. 18, 2006, pp. 359-369.

Rettig et al., "Corrosion resistance studies on grain-boundary etched drug-eluting stents," *J. Mater Sci: Mater Med.*, 2007, vol. 18, pp. 1377-1387.

Rettig et al., "Time-dependent electrochemical characterization of the corrosion of a magnesium rare-earth alloy in simulated body fluids," *Journal of Biomedical Materials Research Part A*, 2007, 167-175.

Rezwan et al., "Biodegradable and bio active porous polymer/inorganic composite scaffolds for bone tissue engineering," *Biomaterials*, 2006, 27:3413-3431.

Rhule et al., "Polyoxometalates in Medicine," *Chem. Rev.*, 1998, 98:327-357.

Rinkevich et al., "Regeneration of Amputated Avian Bone by a Coral Skeletal Implant," *Biol. Bull.*, vol. 197, Aug. 1999, pp. 11-13.

Rivers et al., "Synthesis of a novel, biodegradable electrically conducting polymer for biomedical applications," *Advanced Functional Materials*, 2002, 12: 33-37.

Russell-Stevens et al., "The effect of thermal cycling on the properties of a carbon fibre reinforced magnesium composite," *Materials Science and Engineering A*, 2005, 397: 249-256.

Rutledge et al., "Electrostatic Spinning and Properties of Ultrafine Fibers," *National Textile Center Annual Report*, Nov. 2001, M01-D22, pp. 1-10.

Ryan et al., "Fabrication methods of porous metals for use in orthopaedic applications," *Biomaterials*, 2006, 27:2651-2670.

Sastry et al., "DNA-Mediated Electrostatic Assembly of Gold Nanoparticles into Linear Arrays by a Simple Drop-Coating Procedure," *Appl. Phys. Lett.*, 2001, 78:2943-2945.

Satoh et al., "Effect of Antioxidants on Radical Intensity and Cytotoxic Activity of Eugenol," *Anticancer Res.*, 1998, 18:1549-1552.

Sawitowski et al., "Nanoporous Alumina Coatings for Medical Implants and Stents—Radiotherapy, Drug Delivery, Biological Compatibility," *Materials Research Society Symposium Proceedings*, 1999, 581:523-528.

Sawitowski, "New Drug Delivery Systems—Examples of Applied Nanotechnology," *VDE World Microtechnologies Congress*, Sep. 25-27, 2000, Expo 2000, Hannover, Germany, Proveeds vol. 1, p. 343-346.

Sawyer et al., "Electrochemical Criteria in the Choice of Materials used in Vascular Prostheses," *Biophysical Mechanisms in Vascular Homeostasis and Intravascular Thrombosis*, 1965, pp. 337-348.

Schauer et al., "Protection of iron against corrosion with polyaniline primers," *Progress in Organic Coatings*, 1998, 33: 20-27.

Schetky, "Shape Memory Alloys," *Encyclopedia of Chemical Technology* (3rd ed.), 1982, John Wiley & Sons, 20:726.

Schinhammer et al., "Design strategy for biodegradable Fe-based alloys for medical applications," *Acta Biomaterialia*, 2009, pp. 1-9.

Schmidt et al., "Physiochemical changes in London clay adjacent to cast iron pipes," *IAEG 2006, The Geological Society of London*, Paper 313, 12 pages.

Schneider et al., "From functional core/shell nanoparticles prepared via layer-by-layer deposition to empty nanospheres," *Nano Letters*, 2004, 4: 1833-1839.

Schranz et al., "Bioabsorbable Metal Stents for Percutaneous Treatment of Critical Recoarctation of the Aorta in a Newborn," *Catheterization and Cardiovascular Interventions*, vol. 67, 2006, pp. 671-673.

Secheresse et al., "$(Mo_2O_2X_2)^{2+}$ (X=O,S), a magic building block for the design of wheel shaped metalates," *C.R. Chimie*, 2005, 8: 1927-1938.

Serruys et al., "A bioabsorbable everolimus-eluting coronary stent system (ABSORB): 2-year outcomes and results from multiple imaging methods," *The Lancet*, 2009, 373: 897-910.

Serruys, "Fourth Annual American College of Cardiology International Lecture," *Journal of the American College of Cardiology*, 2006, vol. 47, No. 9, pp. 1754-1768.

Serruys, "Glimpse into the future: bioabsorbable stents—aiming to restore vascular integrity—Introduction & Objectives," *Euro PCR09*, May 18, 2009, pp. 1-4.

Shaw, "Corrosion Resistance of Magnesium Alloys," *ASM Handbook Volume 13A: Corrosion: Fundamentals, Testing, and Protection*. 2003, 5 pages.

Shenoy et al., "Role of Chain Entanglements on Fiber Formation During Electrospinning of Polymer Solutions: Good Solvent, Non-Specific Polymer-polymer Interaction Limit," *Polymer*, 2005, 46:3372-3384.

Shevchenk et al., "Porous Surface of NiTi Alloy Produced by Plasma Ion Implantation," *Institute of Ion Beam Physics and Materials Research*, 2005, Strasbourg, 1 page.

Shevchenko, "Structure, composition and mechanical properties of porous layers produced by argon PIII," *Forschungszentrum Dresden*, Oct. 2007, 8 pages.

Shi et al., "A novel electrically conductive and biodegradable composite made of polypyrrole nanoparticles and polylactide," *Biomaterials*, 2004, 25:2477-2488.

Shieh et al. "Aqueous dispersions of magnetite nanoparticles with NH3 surfaces for magnetic manipulations of biomolecules and MRI contrast agents" *Biomaterials*, 2005 26: 7183-7191.

Shin, "Experimental Characterization of Electrospinning: the Electrically Forced Jet and Instabilities," *Polymer*, 2001, 42:9955-9967.

Sieber, et al., "Investigations on the passivity of iron in borate and phosphate buffers, pH 8.4," *Corrosion Science*, vol. 48, 2006, pp. 3472-3488.

Singh et al., "Electrocatalytic Activity of Electrodeposited Composite Films of Polypyrrole and $CoFe_2O_4$ Nanoparticles Towards Oxygen Reduction Reaction," *Electrochimica Acta*, 2004, 49:4605-4612.

Singh Raman et al., "Laser assisted modification of surface microstructure for localised corrosion resistance of magnesium alloys," *Surface Engineering*, 2007, 23(2):107-111.

Smith et al. "Patterning self-assembled monolayers" *Progress in Surface Science*. 2004. 75:1-68.

Song et al., "Galvanic corrosion of magnesium alloy AZ91D in contact with an aluminium alloy, steel and zinc," *Corrosion Science*, 2004, 46:955-977.

Soto et al., "Amporphous magnesium nitride films produced by reactive pulsed lasar deposition," Journal of Non-Crystalline Solids, 2004, 342: 65-69.

Stoclet et al., "Vascular protection by dietary polyphenols," *Eur. J. Pharmacol.*, 2004, 500:299-313.

Stoner et al., "The mechanism of low frequency a.c. Electrochemical Disinfection," *Bioelectrochemistry and Bioenergetics*, 1982, 9:229-243.

Straumal et al., "Vacuum arc deposition of protective layers on glass and polymer," *Thin Solid Films*, 2001, 383:224-226.

Su et al., "Photoacoustic imaging of coronary artery stents," *Optics Express*, vol. 17, No. 22, Oct. 26, 2009, pp. 1-8.

Suhaj, "Spice antioxidants isolation and their antiradical activity: a review," *J. Food Composition and Analysis*, 2006, 19:531-537.

Sukhorukov et al., "Comparative Analysis of Hollow and Filled Polyelectrolyte Microcapsules Templated on Melamine Formaldehyde and Carbonate Cores," *Macromol. Chem. Phys.*, 2004, 205:530-535.

Sun et al., "Fabrication of a multilayer film electrode containing porphyrin and its application as a potentiometric sensor of iodide ion," *Talanta*, 1998, 46: 15-21.

Suslick et al., "The photochemistry of chromium, manganese, and iron porphytin complexes," J. Chem., 1992, 16:633-642.

Tada et al., "Distribution of pH during galvanic corrosion of a Zn/steel couple," *Electrochimica Acta*, 2004, 49:1019-1026.

Tan et al., "Systematic Parameter Study for Ultra-Fine Fiber Fabrication Via Electrospinning Process," *Polymer*, 2005, 46:6128-6134.

Tian et al., "Corrosion resistance improvement of magnesium alloy using nitrogen plasma ion implantation," *Surface & Coatings Technology*, 2005, 198:454-458.

Truong et al., "Corrosion protection of magnesium by electroactive polypyrrole/paint coatings," *Synthetic Metals*, 2000, 110: 7-15.

Turler et al., "Experimental low-level direct current therapy in liver metastases: influence of polarity and current dose," *Bioelectromagnetics*, 2000, 21(5):395-401.

Uhlmann et al., "Schnelle 3D-Analyse von Gefugemerkmalen" *Druckguss*, Apr. 2009, pp. 1-5.

Van Alst, "Potential conflicts of interest," *Euro PCR09*, 2009, pp. 1-22.

Vermette et al., "Immobilized Liposome Layers for Drug Delivery Applications," *J. Controlled Release*, 2002, 80:179-195.

Virtanen et al., "Electrochemical Behavior of Fe in Phosphate Solutions Studied by In Situ X-Ray Absorption Near Edge Structure," *Journal of the Electrochemical Society*, vol. 146, No. 11, 1999, pp. 4087-4094.

Virtanen et al., "Special modes of corrosion under physiological and simulated physiological conditions," *Acta Biomaterialia*, vol. 4, 2008, pp. 468-476.

Virtanen, "Corrosion of Biomedical Implant Materials," *Corrosion of Biomedical Implant Materials*, vol. 26, Nos. 2-3, 2008, pp. 147-171.

Viswanathamurthi et al., "Preparation and morphology of niobuim oxide fibres by electrospinning," *Chemical Physics Letters*, 2003, 374: 79-84.

Volkova, "Effect of Deformation and Heat Treatment on the Structure and properties of Magnesium Alloys of the Mg—Zn—Zr System," *Metal Science and Heat Treatment*, vo. 48, Nos. 11-12, 2006, pp. 508-512.

Volynova et al., "Mechanical Properties and the Fine Structure of Powdered Iron-Manganese Alloys," *Plenum Publishing Corp.*, 1987, pp. 999-1006.

von Euler et al., "Cell proliferation and apoptosis in rat mammary cancer after electrochemical treatment (EChT)," *Bioelectrochemistry*, 2004, 62:57-65.

Vrbanic et al., "Air-Stable Monodispersed $Mo_6S_3I_6$ Nanowires," *Nanotechnology*, 2004, 15:635-638.

Waksman et al., "Early- and Long-Term Intravascular Ultrasound and Angiographic Findings After Bioabsorbable Magnesium Stent Implantation in Human Coronary Arteries," *JACC: Cardiovascular Interventions*, vol. 2, No. 4, 2009, pp. 1-9.

Waksman et al., "Safety and Efficacy of Bioabsorbable Magnesium Alloy Stents in Procine Coronary Arteries," *Catherterization and Cardiovascular Intervnetions*, 2006, vol. 68, pp. 607-617.

Waksman et al., "Short-term Effects of Biocorrodible Iron Stents in Porcine Coronary Arteries," *Journal of Interventional Cardiology*, vol. 21, No. 1, 2008, pp. 15-20.

Waksman, "Update on Bioabsorbable Stents: From Bench to Clinical," *Journal of Interventional Cardiology*, vol. 19, No. 5, 2006, pp. 414-421.

Waksman, Ron, "Current state of the metallic bioabsorbable stent," Glimpse to the Future, *Euro PCR09*, 2009, pp. 1-24.

Waksman, Ron, "Why Bioabsorbale Stent Technology," Glimpse to the Future, *Euro PCR09*, 2009, pp. 1-16.

Wallerath et al., "A blend of polyphenolic compounds explains the stimulatory effect of red wine on human endothelial NO synthase," *Nitric Oxide*, 2005, 12:97-104.

Wan et al., "Preparation and characterization of porous conducting poly(DL-lactide) composite membrances," *Journal of Membrane Science*, 2005, 246: 193-201.

Wan et al., "Influence of Plasma Immersion Ion Implantation on Corrosion Properties of Magnesium," *Southwest Jiaotong University*, 2005, Chengu, 11 pages.

Wang et al., "Nonlinear optical properties of thin iron films grown on MgO (100) by uplsed laser deposition," *Thin Solid Films*, 2005, 471:86-90.

Wang et al., "Polyaniline microrods synthesized by a polyoxometalates/poly(vinyl alcohol) microfibers template," *Materials Letters*, 2005, 59: 3982-3985.

Weiss et al., "Pyrrole derivatives for electrochemical coating of metallic medical devices," J. Polymer Science, Part A: Polymer Chemistry, 2004, 42: 1658-1667.

Wang, "Recent development of non-platinum catalysts for oxygen reduction reaction," *J. Power Sources*, 2005, 152:1-15.

Weber et al., "Hardness and corrosion resistance of single-phase nitride and carbide on ion," *Materials Science and Engineering*, 1995, 99:205-210.

Weh et al., "Evolution of afractal-like surface structures in layers of polyacrylonitrile solutions by interfacial dynamic processes," *J. Colloid and Interface Science*, 2004, 271: 407-415.

White and Slade, "Polymer electrodes doped with heteropolymetallates and their use within solid-state supercapacitors," *Synthetic Metals*, 2003, 139: 123-131.

Widmer et al., "Manufacture of porous biodegradable polymer conduits by an extrusion process for guided tissue regeneration," *Biomaterials*, 1998, 19:1945-1955.

Wieneke et al., "Stent Coating: A New Approach in Interventional Cardiology," *Herz*, 2002, 27(6):518-526.

Wilcox, "Biodegradable Technology: Medtronic Biodegradable Stent Program," *Euro PCR09*, 2009, pp. 1-25.

Williamson and Manach, "Bioavailability and bioefficacy of polyphenols in humans. II. Review of 93 intervention studies," *Am. J. Clin. Nutr.*, 2005, 81(suppl):243S-255S.

Windecker et al., "Biolimus-eluting stent with biodegradable polymer versus sirolimus-eluting stent with durable polymer for coronary revascularisations (LEADRERS): a randomized non-inferiority trial," *The Lancet*, Sep. 1, 2008, pp. 1-11.

Witte et al., "Biodegradable magnesium-hydroxyapatite metal matrix composites," *Biomaterials*, vol. 28, 2007, pp. 2163-2174.

Witte et al., "In vitro and in vivo corrosion measurements of magnesium alloys," *Biomaterials*, 2006, 27:1013-1018.

Witte et al., "In Vivo Corrosion of Four Magnesium Alloys and the Associated Bone Response," *Biomaterials*, vol. 26, 2005, pp. 3557-3563.

Witte, "The history of biodegradable magnesium implants: A review," *Acta Biomaterialia*, 2010, 6: 1680-1692.

Witte, "Magnesium Corrosion: a New Challaenge for temporary Biomaterials," *Laboratory for Biomechanic and Biomaterials*, 2009, pp. 1-20.

Wuisman and Smit, "Bioresorbable polymers: heading for a new generation of spinal cages," *Eur. Spine J.*, 2006, 15: 133-148.

Xin et al., "Electrochemical Treatment of Lung Cancer," *Bioelectromagnetics*, 1997, 18:8-13.

Xu et al., "In Vivo corrosion behaviouc of Mg—MnZn alloy for bone implant application," *Journal of Biomedical Materials Research Part A*, Jun. 4, 2007, pp. 703-711.

Yamaguchi et al., "Mg2Si Coating Technology on Magnesium Alloys to Improve Corrosion and Wear Resistance", *JOM*, 2004, p. 343.

Ye et al., "In situ synthesis of AIN particles in Mg—Al alloy by $Mg_3$—$N_2$ addition," *Materials Letters*, 2004, 58: 2361-2361.

Yen et al., "Electrochemical treatment of human KB cells in vitro," *Bioelectromagnetics*, 1999, 20:34-41.

Yfantis et al., "Novel corrosion-resistant films for Mg alloys," *Surface and Coatings Technology*, 2002, 151-152: 400-404.

Yi et al., "Characterization of a bioactive nanotextured surface created by controlled chemical oxidation of titanium," *Surface Science*, 2006, 600:4613-4621.

You et al., "The Effect of Calcium Additions on the Oxidation Behavior in Magnesium Alloys," *Scripta mater.*, 2000, 42:1089-1094.

Yu and Uan, "Sacrificial Mg film anode for cathodic protection of die cast Mg-9-wt.%—1 wt.%Zn alloy in NaCl aqueous solution," *Scripta Mat.*, 2006, 54:1253-1257.

Yue et al., "Improvement in the Corrosion Resistance of Magnesium ZK60/SiC Composite by Excimer Laser Surface Treatment," *Scripta Materialia*, 1998, 38(2):191-198.

Yun et al., "Revolutionizing Biodegradable Materials," *Materials Today*, Oct. 2009, vol. 12, No. 10, pp. 1-11.

Zarras et al., "Progress in using conductive polymers as corrosion-inhibiting coatings," *Radiation Physics and Chemistry*, 2003, 68: 387-394.

Zberg et al., "MgZnCa glasses without clinically observable hydrogen evolution for biodegradable implants," *Nature materials*, Sep. 27, 2009, vol. 8, pp. 887-891.

Zeta Potential—An Introduction in 30 Minutes, Technical Note; http://www.nbtc.cornell.edu/facilities/downloads/Zeta%20potential%20-%20An%20introduction%20in%2030%20minutes.pdf, Retrieved from the Internet on May 9, 2005 (6 pages).

Zhang et al., "Improving multilayer films endurance by photoinduced interaction between Dawson-type polyoxometalate and diazo resin," *Materials Chemistry and Physics*, 2005, 90:47-52.

Zhang et al., "Natural Polyelectrolyte Films Based on Layer-by-Layer Deposition of Collagen and Hyaluronic Acid," *Biomaterials*, 2005, 26:3353-3361.

Zhang et al., "Ways for fabricating stable layer-by later self-asemblies: combined ionic self-assembly and post chemical reaction," *Colloids and Surfaces A: physiochemical and Engineering Aspects*, 2002, pp. 198-200, 439-442.

Zheng, "Symposium on Biodegradable/Biocorroded metallic materials," Nov. 24, 2009, pp. 1-74.

Zhou et al., "Drug-loaded, Magnetic, hollow silica nanocomposites for nanomedicine," *Nanomedicine: Nanotechnology, Biology and Medicine*, 2005, 1:233-237.

Zhu et al., "Biocompatibility of Fe—O films synthesized by plasma immersion ion implantation and deposition," *Surface and Coatings Technology*, vol. 203, 2009, pp. 1523-1529.

Zhu et al., "Biocompatibility of pure iron: In Vitro assessment of degradation kinetics and cytotoxicity on endothelial cells," *Materials Science and Engineering*, vol. 29, 2009, pp. 1589-1582.

Zou et al., "Preparation of a phosophopolyoxomolybdate $P_2Mo_{18}O^{6-}_{62}$ doped polypyrrole modified electrode and its catalytic properties," *Journal of Electroanalytical Chemistry*, 2004, 566: 63-71.

Zucchi et al., "Electrochemical behaviour of a magnesium alloy containing rare earth elements," *Journal of Applied Electrochemistry*, 2006, vol. 36, pp. 195-204.

Zucchi et al., "Influence of a silane treatment on the corrosion resistance of a WE43 magnesium alloy," *Surface Coatings Technol.*, 2006, 200:4136-4143.

International Search Report and Written Opinion from PCT/US09/043591, mailed Jun. 30, 2010, 10 pages.

International Search Report from PCT/US07/005671, mailed Jun. 2, 2008, 10 pages.

Ma et al., "Inhibition effect of self-assembled films formed by gold nonoparticles on iron surface," *Applied Surface Science*, 2006, 252: 4327-4334.

Li et al., "The corrosion inhibition of the self assembled Au, and Ag nonoparticles films on the surface of copper," Colloids and Surfaces A: Physiochem. Eng. Aspects, 2006, 273: 16-23.

International Preliminary Report on Patentability from PCT/US08/75976 dated Mar. 25, 2010, mailed Nov. 25, 2008, 8 pages.

International Preliminary Report on Patentability from PCT/US09/043326 mailed Nov. 18, 2010, 7 pages.

International Search Report from PCT/US09/051965 mailed Aug. 20, 2010, 13 pages.

International Preliminary Report on Patentability from PCT/US09/051965 mailed Feb. 10, 2011, 8 pages.

International Preliminary Report on Patentability in PCT/US09/49422 mailed Jan. 13, 2011, 7 pages.

International Preliminary Report on Patentability from PCT/US2010/042772 mailed Feb. 4, 2011, 9 pages.

International Preliminary Report on Patentability in PCT/US2009/43326 mailed Nov. 18, 2010, 7 pages.

International Preliminary Report on Patentability in PCT/US09/046750 mailed Dec. 23, 2010, 8 pages.

Deepwater, "Galvanic Series," http://corrosion-doctors.org/definitions/galvanic-series.htm> on Mar. 11, 2011, 5 pages.

Wikipedia, the Free Encyclopedia, "Galvanic Corrosion." <http://en.wikipedia.org/wiki/Galvanic_corrosion> on Mar. 11, 2011, 7 pages.

International Search Report from PCT/US2010/060412 mailed Feb. 21, 2011, 10 pages.

Dumas et al., "Characterization of magnesium fluoride thin films produced by argon ion beam-assisted deposition," *Thin Solid Films*, 2001, pp. 61-68.

International Preliminary Report on Patentability from PCT/US09/059424, mailed May 5, 2011, 8 pages.

US 6,533,715, 03/2003, Hossainy et al. (withdrawn)

* cited by examiner

BIOABSORBABLE METAL MEDICAL DEVICE AND METHOD OF MANUFACTURE

FIELD OF THE INVENTION

The present invention relates generally to cutting, welding, brazing and ablation techniques, and more specifically to techniques that employ a laser/fluid jet to cut, weld, braze or ablate bioabsorbable metal medical devices such as stents.

BACKGROUND OF THE INVENTION

Stents and stent delivery devices are employed in a number of medical procedures and as such their structure and function are well known. Stents are used in a wide array of bodily vessels including coronary arteries, renal arteries, peripheral arteries including iliac arteries, arteries of the neck and cerebral arteries as well as in other body structures, including but not limited to arteries, veins, biliary ducts, urethras, fallopian tubes, bronchial tubes, the trachea, the esophagus and the prostate.

Stents are typically cylindrical, radially expandable prostheses introduced via a catheter assembly into a lumen of a body vessel in a configuration having a generally reduced diameter, i.e. in a crimped or unexpanded state, and are then expanded to the diameter of the vessel. In their expanded state, stents support or reinforce sections of vessel walls, for example a blood vessel, which have collapsed, are partially occluded, blocked, weakened, or dilated, and maintain them in an open unobstructed state. To be effective, the stent should be relatively flexible along its length so as to facilitate delivery through torturous body lumens, and yet stiff and stable enough when radially expanded to maintain the blood vessel or artery open. Such stents may include a plurality of axial bends or crowns adjoined together by a plurality of struts so as to form a plurality of U-shaped members coupled together to form a serpentine pattern.

There are two types of stents that are presently utilized: permanent stents and bioabsorbable stents. A permanent stent is designed to be maintained in a body lumen for an indeterminate amount of time. Permanent stents are typically designed to provide long-term support for damaged or traumatized wall tissues of the lumen. There are numerous conventional applications for permanent stents including cardiovascular, peripheral, urological, gastrointestinal, and gynecological applications.

Bioabsorbable stents may advantageously be eliminated from body lumens after a predetermined, clinically appropriate period of time, for example, after the traumatized tissues of the lumen have healed and a stent is no longer needed to maintain the integrity of the lumen. The conventional bioabsorbable materials from which such stents are made are selected to resorb or degrade over time, thereby eliminating the need for subsequent surgical procedures to remove the stent from the body lumen if problems arise.

One technique that is employed to manufacture stents is laser cutting. Laser cutting of stents has been described in a number of publications including U.S. Pat. No. 5,780,807 to Saunders, U.S. Pat. No. 5,922,005 to Richter and U.S. Pat. No. 5,906,759 to Richter. Laser cutting usually involves the use of a pulsed laser beam and a stent preform such as a tubular preform that is positioned under the laser beam and moved in a precise manner to cut a desired pattern into the preform using a servo motion controlled machine tool. Laser cutting is sometimes performed in an oxygen atmosphere to assist in the process. An example of a conventional laser for cutting a stent is a highly focused pulsed Nd:YAG laser which has a pulse duration in the range of approximately 0.1 to 20 milliseconds. The laser produces a relatively large melt zone and heat affected zone (HAZ) on the metal.

To reduce the size of the heat affected zone, cutting and processing systems have been developed that incorporate a water column and laser. For example, SYNOVA Inc., of Lausanne, Switzerland, has developed a laser-microjet that uses a laser beam that is contained within a water jet arranged as a parallel beam, similar in principle to an optical fiber. The SYNOVA laser-microjet relies on a low pressure water column to contain the laser, to reduce force applied to the work piece, to act as a cooling mechanism and to remove cutting debris. In U.S. Pat. No. 6,696,666, a laser microjet is employed to manufacture a stent. A second water jet is directed through the tubular preform to deflect the laser beam, thereby preventing damage to the interior wall of the tubular preform.

SUMMARY OF THE INVENTION

In accordance with the present invention, a method and apparatus is provided for processing a medical device formed from a bioabsorbable metallic material. The method begins by generating a beam of radiation onto the bioabsorbable metallic material. The radiation beam is transmitted through a fluid medium and onto a heat affected zone (HAZ) of the bioabsorbable metallic material to thereby cool the HAZ and reduce a concentration of oxygen surrounding the HAZ.

In accordance with one aspect of the invention, the bioabsorbable material is a magnesium alloy.

In accordance with another aspect of the invention, the magnesium alloy is selected from the group consisting of lithium-magnesium and sodium-magnesium.

In accordance with another aspect of the invention, the magnesium alloy includes a rare-earth element.

In accordance with another aspect of the invention, the magnesium alloy includes yttrium.

In accordance with another aspect of the invention, a proportion of magnesium in the alloy is greater than about 90%.

In accordance with another aspect of the invention, the fluid medium comprises a fluid column that is parallel to the radiation beam.

In accordance with another aspect of the invention, the radiation beam and the fluid column comprise a laser/fluid jet.

In accordance with another aspect of the invention, the fluid comprises water.

In accordance with another aspect of the invention, the fluid includes a dissolved gas that displaces dissolved oxygen.

In accordance with another aspect of the invention, the radiation is applied to cut the material.

In accordance with another aspect of the invention, the radiation is applied to weld or braze together first and second components of the material.

In accordance with another aspect of the invention, the radiation provides a surface treatment to the material In accordance with another aspect of the invention, the material is a tubular preform.

In accordance with another aspect of the invention, the medical device is a stent.

In accordance with another aspect of the invention, the medical device is a filter device.

In accordance with another aspect of the invention, the radiation beam is generated by a laser source.

DETAILED DESCRIPTION

Figure 1:
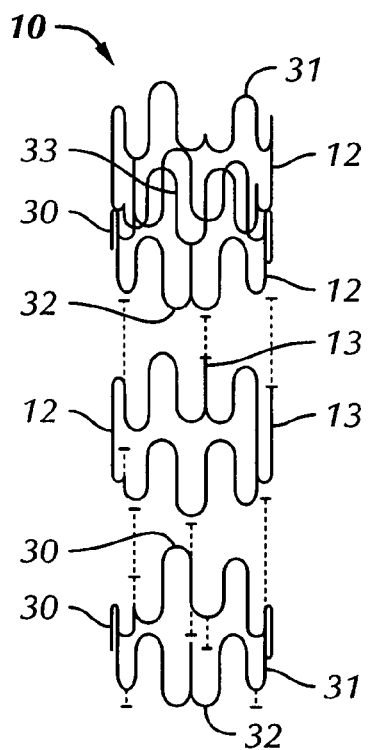
FIG. 1 shows in fragment a portion of an exemplary stent that may be manufactured in accordance with the present invention.

The present invention applies laser processing techniques to fabricate from a bioabsorbable metallic material a wide variety of medical devices including, without limitation, stents, filter devices (e.g. vena cava filters, carotid and cardiac embolic protection filters), neurovascular coils, electrical stimulation leads, and the like. As discussed in detail below, a fluid is applied to the heat affected zone (HAZ) of a magnesium alloy-based material to prevent the magnesium from igniting by cooling the material and displacing oxygen surrounding the HAZ. For purposes of illustration only and not as a limitation on the invention, the present invention will be described in terms of stents formed from a cylindrical metal mesh that can expand when pressure is internally applied. One example of such a stent, described below, is shown in FIG. 1. Of course, the present invention is equally applicable to a wide variety of other types of stents including, without limitation, various balloon-expandable and self-expanding stents, as well as those formed from a sheet or tube into spiral, coil or woven geometries, either open or closed cell.

The present invention may be employed in a variety of different laser or other electromagnetic radiation processing techniques that includes but is not limited to laser cutting techniques. For example, the invention is applicable to laser welding, and laser brazing techniques in which a laser or other electromagnetic beam is applied to a joint for the purpose of securing one element of a medical device, such as the strut of a stent, for example, to another element of the bioabsorbable medical device such as another strut. The invention is also applicable to laser ablation techniques to provide a surface treatment such as texturing roughening, polishing, and the like or to form a feature on or within any portion of the bioabsorbable medical device.

Having reference to FIG. 1, there is shown an exemplary bioabsorbable stent 10. The stent generally comprises a plurality of radially expandable cylindrical elements 12 disposed generally coaxially and interconnected by elements 13 disposed between adjacent cylindrical elements 12. The cylindrical elements 12 have an undulating pattern. The particular pattern and number of undulations per unit of length around the circumference of the cylindrical element 12, or the amplitude of the undulations, are chosen to fill particular mechanical requirements for the stent 10 such as radial stiffness.

Each pair of the interconnecting elements 13 on one side of a cylindrical element 12 can be placed to achieve maximum flexibility for a stent. In this example the stent 10 has three interconnecting elements 13 between adjacent radially expandable cylindrical elements 12, which are 120 degrees apart. Each pair of interconnecting elements 13 on one side of a cylindrical element 12 are offset radially 60 degrees from the pair on the other side of the cylindrical element. The alternation of the interconnecting elements 13 results in a stent that is longitudinally flexible in essentially all directions. Various other configurations for the placement of interconnecting elements 13 are possible. However, the interconnecting elements 13 of an individual stent typically should be secured to either the peaks or valleys of the undulating structural elements 12 in order to prevent shortening of the stent during the expansion thereof. Additional details concerning the particular stent depicted in FIG. 1 as well as variations thereof are shown, for example, in U.S. Pat. No. 5,514,154.

The bioabsorbable stent 10 is formed of a bioabsorbable metal alloy. Bioabsorbable metal alloys useful for stents include zinc-titanium alloys, and magnesium alloys, such as lithium-magnesium, sodium-magnesium, and magnesium alloys containing rare earth metals. Some examples of bioabsorbable metal alloys are described in U.S. Pat. No. 6,287,332 and U.S. Appl. Serial No. 2004/0220660.

As discussed in U.S. Appl. Serial No. 2004/0098108, one particular magnesium alloy that may be employed has a magnesium proportion greater than 90%. In addition the magnesium alloy contains yttrium in a proportion of between 4% and 5% and neodymium as a rare earth element in a proportion of between 1.5% and 4%. The remaining constituents of the alloy are less than 1% and are formed for the major part by lithium or zirconium.

If lithium-magnesium alloys are employed, lithium hydroxide and magnesium hydroxide are to be expected as decomposition products, which can both be considered non-toxic and biocompatible. However, these decomposition products are poorly soluble and, with the absorption of carbon dioxide convert to carbonates, which are also poorly soluble. To overcome this problem, other combinations of magnesium alloys may be employed, such as a sodium-magnesium alloy, for example. Sodium hydroxide possesses a high solubility and the sodium dissolves. The other decomposition product, magnesium hydroxide, forms a fine precipitate that may deposit without risk in the developing vascular skin.

One problem that arises when laser cutting is used to form a magnesium alloy stent is that the alloy easily oxidizes and combusts readily. This problem is exacerbated since laser cutting is often performed in an oxygen atmosphere. To overcome this problem, the present invention employs a fluid during the cutting process to both cool the cutting area and reduce the oxygen concentration in the cutting zone. The combination of cooling and oxygen isolation can prevent the magnesium from igniting. In some cases the dissolved oxygen content should be less than about 0.5 mg/L.

Figure 2:
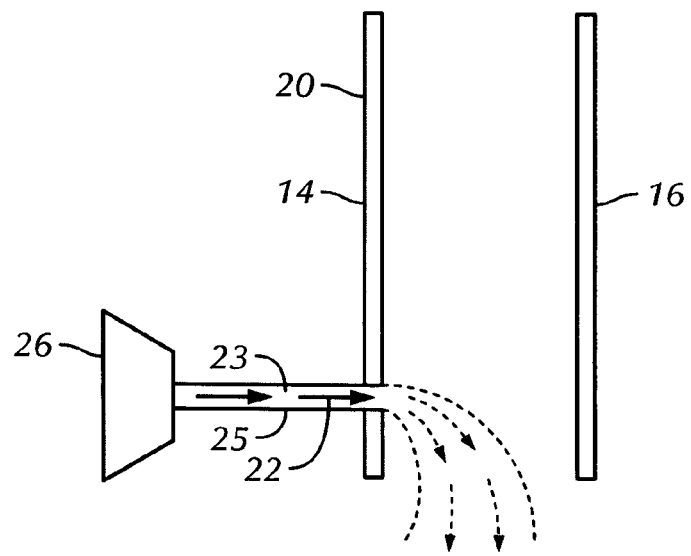
FIG. 2 is a cut-away schematic representation of one example of a cutting and processing system that incorporates a fluid column and a laser.

FIG. 2 shows a system for processing and/or cutting a stent preform 20 using a laser beam. The stent preform 20 may be in the form of a tube (as shown), a sheet or any other shape of material into which a stent design is cut. The preform 20 is processed or cut by the application of laser energy, indicated by arrow 22. Laser energy 22 is transmitted through a column or stream of water or other solution or fluid referred to hereinafter as a fluid column 23. Fluid column 23 behaves similarly to a fiber optic in that the fluid column 23 allows the laser energy 22 to be focused and transmitted therethrough. The combined stream of laser energy 22 and water or fluid column 23 is collectively referred to herein as a jet 25. As previously mentioned, the use of a hybrid laser/water jet for the purpose of cutting is known and laser/water jet mechanisms are commercially available from SYNOVA Inc., of Lausanne, Switzerland.

As is shown in FIG. 2, jet 25 is directed to the exterior of the processing side 14 of the tubular preform 20. Jet 25 is supplied by a laser-jet mechanism 26 such as is available from SYNOVA Inc. Mechanism 26 includes a laser, which may be any type of laser suitable for use in processing tubular members. For example, laser energy 22 may be energy that is supplied by a YAG laser, IR laser, UV laser, $CO_2$ laser, diode laser, etc. or any combination thereof.

In addition to providing a natural cooling mechanism as well as aiding in drawing debris away from the cutting site, the fluid column 23 creates an envelope around the cutting site to expel oxygen and prevents an oxygen concentration buildup great enough to allow the magnesium from igniting.

The fluid column 23 may be composed of a variety of substances. For example, fluid column 23 may be primarily water, mineral oil, and the like. While a wide range of fluids may be employed, those that are highly flammable such as gasoline and toluene should be avoided. If water is employed, it should have a relatively low level of dissolved oxygen in it. In this regard it may be helpful to add dissolved $CO_2$ (or another gas such as an inert gas) into the water so that oxygen is displaced, thereby further preventing ignition.

In some cases, fluid column 23 may be a stream of liquid having $CO_2$ or other gaseous bubbles and/or micro-bubbles therein. In yet another example, fluid column may be a solution of liquid having material dissolved therein, such that the resulting solution has some degree of energy reflecting and/or absorbing characteristics.

Laser energy 22 may be provided, for example, by a Nd:YAG or $CO_2$ laser operating at a wavelength of, e.g., 1,064 nm and 10,600 nm, respectively. The particular wavelength that is selected should be matched to the fluid so that its transmittance through the fluid is maximized, or is at least sufficiently great to perform the cutting or other processing task. For the fluids mentioned above these wavelengths will generally range from visible to infrared wavelengths (i.e., about 400 nm to 3 microns). The laser source may be an ultra-fast laser operating on a femtosecond or picosecond timescale. Alternatively, a laser operating at a wavelength of about 193 nm or 248 nm or laser diodes such as those operating at wavelengths between about 800 to 1000 nm may be employed. In some embodiments, diode pumped fiber laser may be employed in which the diode provides energy to pump or stimulate a gain element such as a rare-earth element doped in the fiber. The present invention, however, is not limited to laser sources. More generally, any other appropriate source of electromagnetic energy that is capable of cutting or otherwise processing a preform may be employed in the present invention.

Other operational parameters of the laser jet mechanism 26 may be adjusted as known in the art to yield optimal cutting or other processing results. Generally speaking, with respect to the intensity of the energy, an intensity of greater than about $10^6$ Watts/$cm^2$ will be required for cutting while an intensity of greater than about $10^3$ Watts/$cms^2$ will be required for welding.

In some embodiments of the invention, instead, or in addition to the use of a fluid jet, the preform may be submerged in a fluid bath to achieve the necessary cooling and oxygen deprivation. While in these cases, the use of the fluid jet may not be necessary, it may nevertheless be advantageous to facilitate the removal from the cutting zone of particles or molten material that has been ablated from the preform. If employed, the particular fluid used in the fluid jet may or may not be the same as the fluid used in the fluid bath. For instance, in some cases it may be desirable to use a fluid for the jet that has a higher refractive index than the fluid in the bath so that it acts as a waveguide for the laser beam.

The invention claimed is:

1. A method of processing a medical device formed from a bioabsorbable metallic material, comprising:
   generating a beam of radiation onto the bioabsorbable metallic material, the radiation beam creating a heat affected zone (HAZ);
   providing a liquid;
   reducing an oxygen concentration in the liquid to below about 0.5 mg/L; and
   transmitting a fluid column of the liquid around the radiation beam onto the HAZ to thereby cool the HAZ and reduce a concentration of oxygen surrounding the HAZ, wherein the fluid column is parallel to the radiation beam.

2. The method of claim 1 wherein the bioabsorbable material is a magnesium alloy.

3. The method of claim 2 wherein the magnesium alloy is selected from the group consisting of lithium-magnesium and sodium-magnesium.

4. The method of claim 2 wherein the magnesium alloy includes a rare-earth element.

5. The method of claim 2 wherein the magnesium alloy includes yttrium.

6. The method of claim 2 wherein a proportion of magnesium in the alloy is greater than about 90%.

7. The method of claim 1 wherein the radiation beam and the fluid column comprise a laser/fluid jet.

8. The method of claim 1 wherein the liquid comprises water.

9. The method of claim 8 wherein the water includes a dissolved gas that displaces dissolved oxygen.

10. The method of claim 1 wherein the radiation is applied to cut the material.

11. The method of claim 1 wherein the radiation is applied to weld or braze together first and second components of the material.

12. The method of claim 1 wherein the radiation provides a surface treatment to the material.

13. The method of claim 1 wherein the material is a tubular preform.

14. The method of claim 1 wherein the medical device is a stent.

15. The method of claim 1 wherein the medical device is a filter device.

16. The method of claim 1 wherein the radiation beam is generated by a laser source.

17. A method of processing a medical device formed from a bioabsorbable metallic material, comprising:
   generating a beam of radiation onto the bioabsorbable metallic material, the radiation beam creating a heat affected zone (HAZ);
   providing a liquid;
   dissolving a gas into the liquid to thereby reduce the oxygen concentration therein to below about 0.5 mg/L; and
   transmitting a fluid column of the liquid around the radiation beam onto the HAZ to thereby cool the HAZ and reduce a concentration of oxygen surrounding the HAZ, wherein the fluid column is parallel to the radiation beam.

18. The method of claim 17 wherein the gas is an inert gas.

19. The method of claim 17 wherein the gas is $CO_2$.

20. A method of processing a medical device formed from a bioabsorbable metallic material, comprising:
   generating a beam of radiation onto the bioabsorbable metallic material, the radiation beam creating a heat affected zone (HAZ);
   providing a liquid, wherein the liquid is mineral oil, the liquid having an oxygen concentration below about 0.5 mg/L; and
   transmitting a fluid column of the liquid around the radiation beam onto the HAZ to thereby cool the HAZ and reduce a concentration of oxygen surrounding the HAZ, wherein the fluid column is parallel to the radiation beam.

* * * * *